US012421204B2

(12) United States Patent
Kamboj et al.

(10) Patent No.: US 12,421,204 B2
(45) Date of Patent: Sep. 23, 2025

(54) PROCESS FOR PREPARING CHROMAN COMPOUNDS

(71) Applicant: LUPIN LIMITED, Mumbai (IN)

(72) Inventors: Rajender Kumar Kamboj, Pune (IN); Shaji George Kochumalayil, Bangalore (IN); Spinvin Venugopal, Kochi (IN); Kamlesh Jyotindra Padiya, Pune (IN); Prabakaran Kamalakannan, Pune (IN); Kumar Ram Naik, Pune (IN); Sachin Subhash Ingawale, Pune (IN); Bhavani Shankar Rajesh, Pune (IN); Rajendra Ganpati Powar, Pune (IN)

(73) Assignee: LUPIN LIMITED, Mumbai (IN)

( * ) Notice: Subject to any disclaimer, the term of this patent is extended or adjusted under 35 U.S.C. 154(b) by 736 days.

(21) Appl. No.: 17/778,282

(22) PCT Filed: Nov. 18, 2020

(86) PCT No.: PCT/IN2020/050965
§ 371 (c)(1),
(2) Date: May 19, 2022

(87) PCT Pub. No.: WO2021/100059
PCT Pub. Date: May 27, 2021

(65) Prior Publication Data
US 2023/0025246 A1 Jan. 26, 2023

(30) Foreign Application Priority Data
Nov. 19, 2019 (IN) .............................. 201921047127

(51) Int. Cl.
C07D 311/58 (2006.01)

(52) U.S. Cl.
CPC ........ C07D 311/58 (2013.01); C07B 2200/13 (2013.01)

(58) Field of Classification Search
CPC .................................................. C07D 311/58
See application file for complete search history.

(56) References Cited

U.S. PATENT DOCUMENTS

| 5,318,988 A | 6/1994 | Schohe-Loop |
| 2007/0117823 A1 | 5/2007 | Antel |

FOREIGN PATENT DOCUMENTS

| WO | WO 2008/064827 A2 | 6/2008 |
| WO | WO 2013/124828 A1 | 8/2013 |

OTHER PUBLICATIONS

International Search Report and Written Opinion of International Searching Authority for Application No. PCT/IN2020/050965, mailed May 3, 2021 (16 pages).

(Continued)

Primary Examiner — Valerie Rodriguez-Garcia
(74) Attorney, Agent, or Firm — Nixon Peabody LLP; Ravinderjit S. Braich

(57) ABSTRACT

A process for manufacturing substituted chroman compounds in an economically scalable manner, without the use of pyrophoric reagents. Also disclosed herein are chroman compound synthesis routes that do not include column chromatography purification steps. The disclosure also relates to the intermediates used in the synthesis. In particular, the disclosure relates to the synthesis of the Calcium sensing receptor (CaSR) modulating agent 2-methyl-5-((2R,4S)-2-((((R)-1-(naphthalen-1-yl)ethyl)amino)methyl)chroman-4-yl)benzoic acid, its intermediates and pharmaceutically acceptable salts thereof.

10 Claims, 3 Drawing Sheets

(56) References Cited

OTHER PUBLICATIONS

Alvey, L. et al.; "Diversity-oriented synthesis of furo[3,2-f]chromanes with antimycobacterial activity"; European Journal of Medicinal Chemistry, vol. 44, No. 6, pp. 2497-2505; 2009; XP026049347; ISSN: 0223-5234; DOI: 10.1016/J.EJMECH.2009.01.017 (9 pages).
Seidel, D. et al.; "Synthesis of [14C]-labelled repinotan hydrochloride and its major metabolite M-6"; Journal of Labelled Compounds and Radiopharmaceuticals, vol. 45, No. 13, pp. 1115-1132; 2002; XP055779025; ISSN: 0362-4803; DOI: 10.1002/jlcr.629 (18 pages).
Greene, T.W. et al.; *Greene's Protective Groups in Organic Chemistry, Fourth Edition*; John Wiley & Sons; 1999; copyright 2007; ISBN-13: 978-0-471-69754-1; ISBN-10: 0-471-69754-0 (1112 pages).

PROCESS FOR PREPARING CHROMAN COMPOUNDS

CROSS-REFERENCE TO RELATED APPLICATIONS

This application is a U.S. National Stage of International Application No. PCT/IN2020/050965, filed Nov. 18, 2020, which claims priority to and the benefit of Indian Provisional Patent Application No. 201921047127, filed Nov. 19, 2019, the contents of which are hereby incorporated by reference herein in their entireties .

FIELD

This disclosure relates to a process for manufacturing substituted chroman compounds. More specifically, the efficient and safe synthesis of the Calcium sensing receptor (CaSR) modulating agent 2-methyl-5-((2R,4S)-2-((((R)-1-(naphthalen-1-yl)ethyl)amino)methyl)chroman-4-yl)benzoic acid, its intermediates and pharmaceutically acceptable salts thereof are described. Also described are efficient methods of purification of in an economically scalable manner of 2-methyl-5-((2R,4S)-2-((((R)-1-(naphthalen-1-yl)ethyl)amino)methyl)chroman-4-yl)benzoic acid, its intermediates and pharmaceutically acceptable salts thereof. The steps described herein are performed without the use of pyrophoric reagents and without column chromatography purification steps. The invention also relates to the intermediates used in the synthesis. In particular, the invention relates to the synthesis of the Calcium sensing receptor (CaSR) modulating agent 2-methyl-5-((2R,4S)-2-((((R)-1-(naphthalen-1-yl)ethyl)amino)methyl)chroman-4-yl)benzoic acid, its intermediates and pharmaceutically acceptable salts thereof.

BACKGROUND

The following includes information that may be useful in understanding the invention. It is not an admission that any of the information, publications or documents specifically or implicitly referenced herein is prior art, or essential, to the described or claimed invention. All publications and patents mentioned herein are hereby incorporated by reference in their entirety.

Calcium-sensing receptor is a class C G-protein-coupled receptor (GPCR). It plays a major role in the maintenance of a physiological serum ionized calcium (Ca2+) concentration by regulating the circulating levels of parathyroid hormone. Extracellular Ca2+($[Ca^{2+}]_o$) is the primary physiological ligand for CaSR.

Small molecules that are positive allosteric modulators of GPCRs called calcimimetics, modulate and improve the receptor's sensitivity to the already existing milieu of extracellular ionic calcium and reduces PTH secretion. Modulation of GPCRs has been explored as a potential therapy for hyperparathyroidism and diseases associated with decreased CaSR signaling. Cinacalcet was the first CaSR modulating agent to be approved by the U.S. Food and Drug Administration (FDA). Other molecules that can modulate CaSR are also known as described in WO2013/124828.

WO2013/124828 discloses a series of substituted chroman compounds for CaSR modulation. One specific compound disclosed therein is 2-methyl-5-((2R,4S)-2-((((R)-1-(naphthalen-1-yl)ethyl)amino)methyl)chroman-4-yl) benzoic acid hydrochloride. The application also describes a general method of synthesis of these substituted chroman compounds. The drawbacks of the method described in the application include the use of pyrophoric reagents, which are dangerous and therefore not feasible for large-scale use, and purification techniques such as flash chromatography and costly chiral chromatographic techniques for the separation of compounds. The synthesis also includes harsh hydrogenation reaction conditions, which are responsible for formation of unwanted impurities.

In light of the above, there is a need for a more efficient process that is not only more economical but also, at the same time, uses less hazardous reagents for the preparation of 2-methyl-5-((2R,4S)-2-((((R)-1-(naphthalen-1-yl)ethyl)amino)methyl)chroman-4-yl)benzoic acid hydrochloride.

The invention disclosed herein overcomes such limitations whereby 2-methyl-5-((2R,4S)-2-((((R)-1-(naphthalen-1-yl)ethyl)amino)methyl)chroman-4-yl)benzoic acid and its pharmaceutically acceptable salts, as well as the intermediates in the synthesis, can be prepared on an industrial scale without the use of complex or lengthy purification procedures and also with high purity.

SUMMARY

The invention described and claimed herein have many attributes and aspects including, but not limited to, those set forth or described or referenced in this Summary. It is not intended to be all-inclusive and the invention described and claimed herein are not limited to or by the features or embodiments identified in this Summary, which is included for purposes of illustration only and not restriction.

In some aspects, this disclosure provides for a synthesis route of 2-methyl-5-((2R,4S)-2-((((R)-1-(naphthalen-1-yl) ethyl)amino)methyl)chroman-4-yl)benzoic acid and its pharmaceutically acceptable salts, as well as the intermediates in the synthesis, which can be prepared on an industrial scale without the use of complex or lengthy purification procedures and also with high purity with less than about 1.0% of 2-methyl-5-((2R,4R)-2-((((R)-1-(naphthalen-1-yl) ethyl)amino)methyl) chroman-4- yl)benzoic acid hydrochloride (Compound-B) impurity, specifically less than about 0.5% of 2-methyl-5-((2R,4R)-2-((((R)-1-(naphthalen-1-yl)ethyl)amino)methyl) chroman-4- yl) benzoic acid hydrochloride impurity, more specifically less than about 0.2% of 2-methyl-5-((2R,4R)-2-((((R)-1-(naphthalen-1-yl) ethyl)amino)methyl) chroman-4- yl) benzoic acid hydrochloride impurity.

The processes and methods disclosed herein are cost-effective, involve the use of reagents that are mild and easy to handle, and are hence advantageous even when preparing compounds on a large, industrial scale. Also, these processes and methods do not use complex or lengthy purification procedures, but are able to synthesize compounds of high quality and high purity, with less than about 1.0% of 2-methyl-5-((2R,4R)-2-((((R)-1-(naphthalen-1-yl)ethyl) amino)methyl) chroman-4- yl) benzoic acid hydrochloride (Compound-B) impurity, specifically less than about 0.5% of 2-methyl-5-((2R,4R)-2-((((R)-1-(naphthalen-1-yl)ethyl) amino)methyl) chroman-4- yl) benzoic acid hydrochloride impurity, more specifically less than about 0.2% of 2-methyl-5-((2R,4R)-2-((((R)-1-(naphthalen-1-yl)ethyl) amino)methyl) chroman-4- yl) benzoic acid hydrochloride impurity.

In some aspects, the invention advantageously provides for a process for the preparation of 2-methyl-5-((2R,4S)-2-((((R)-1-(naphthalen-1-yl)ethyl)amino)methyl)chroman-4-yl)benzoic acid and its pharmaceutically acceptable salt.

In some aspects, the invention provides for a process for the preparation of 2-methyl-5-((2R,4S)-2-((((R)-1-(naphthalen-1-yl)ethyl)amino)methyl) chroman-4-yl)benzoic acid (Compound-4).

In some aspects, the invention provides for a process for the preparation of 2-methyl-5-((2R,4S)-2-((((R)-1-(naphthalen-1-yl)ethyl)amino)methyl) chroman-4-yl)benzoic acid hydrochloride (Compound-A).

In some aspects, the invention provides for a process for the preparation of 2-methyl-5-((2R,4S)-2-((((R)-1-(naphthalen-1-yl)ethyl)amino)methyl) chroman-4-yl)benzoic acid hydrochloride without using any chromatography steps for its isolation/purification.

In some aspects, the invention provides for a process for the production of 2-methyl-5-((2R,4S)-2-((((R)-1-(naphthalen-1-yl)ethyl)amino)methyl) chroman-4-yl)benzoic acid hydrochloride (Compound-A) having less than about 1.0% of 2-methyl-5-((2R,4R)-2-((((R)-1-(naphthalen-1-yl)ethyl)amino)methyl) chroman-4- yl) benzoic acid hydrochloride (Compound-B) impurity, specifically less than about 0.5% of 2-methyl-5-((2R,4R)-2-((((R)-1-(naphthalen-1-yl)ethyl)amino)methyl) chroman-4- yl) benzoic acid impurity, more specifically less than about 0.2% of 2-methyl-5-((2R,4R)-2-((((R)-1-(naphthalen-1-yl)ethyl)amino)methyl) chroman-4- yl) benzoic acid impurity.

Compound-B

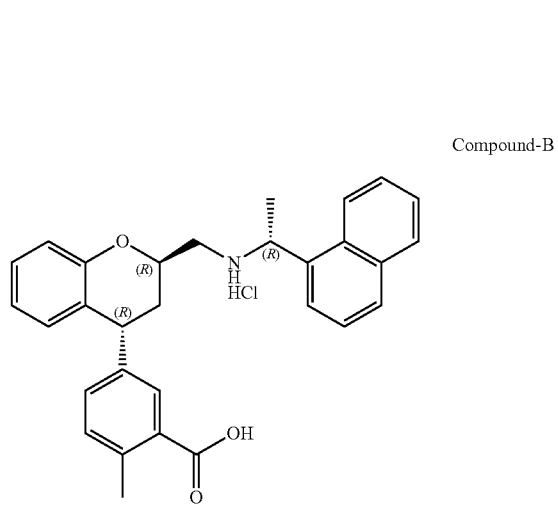

In some aspects, the invention provides for a process for the manufacturing of 2-methyl-5-((2R,4S)-2-((((R)-1-(naphthalen-1-yl)ethyl)amino)methyl) chroman-4-yl)benzoic acid hydrochloride (Compound-A) having less than about 1.0% of 2-methyl-5-((2R,4R)-2-((((R)-1-(naphthalen-1-yl)ethyl)amino)methyl) chroman-4- yl) benzoic acid hydrochloride (Compound-B) impurity, specifically less than about 0.5% of 2-methyl-5-((2R,4R)-2-((((R)-1-(naphthalen-1-yl)ethyl)amino)methyl) chroman-4- yl) benzoic acid impurity, more specifically less than about 0.2% of 2-methyl-5-((2R,4R)-2-((((R)-1-(naphthalen-1-yl)ethyl)amino)methyl) chroman-4- yl) benzoic acid impurity wherein a crystallisation procedure is used.

In some aspects, the invention provides for a process for the manufacture of 2-methyl-5-((2R,4S)-2-((((R)-1-(naphthalen-1-yl)ethyl)amino)methyl) chroman-4-yl)benzoic acid hydrochloride (Compound-A) starting from methyl 5-((R)-2-(((tert-butoxycarbonyl)((R)-1-(naphthalen-1-yl)ethyl)amino)methyl)-2H-chromen-4-yl)-2-methylbenzoate (Compound-1) following the steps comprising:

a) reducing methyl 5-((R)-2-(((tert-butoxycarbonyl)((R)-1-(naphthalen-1-yl)ethyl)amino)methyl)-2H-chromen-4-yl)-2-methylbenzoate (Compound-1) using Pd/C and ammonium formate to give methyl 5-((2R)-2-(((tert-butoxycarbonyl)((R)-1-(naphthalen-1-yl)ethyl)amino) methyl) chroman-4-yl)-2-methylbenzoate (Compound-2)

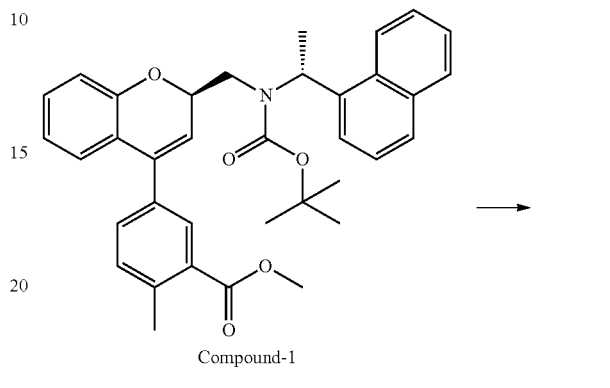

Compound-1

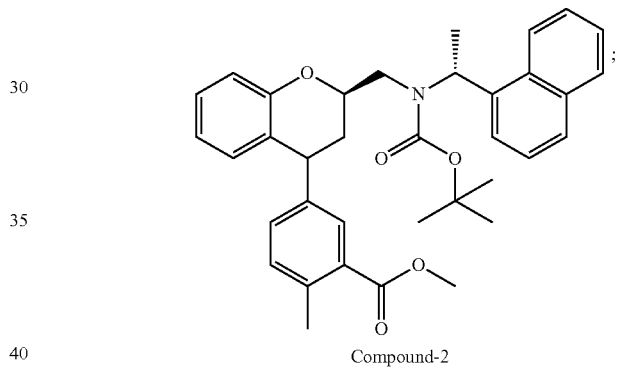

Compound-2 b) carrying out a Boc-deprotection reaction of Compound-2 to give corresponding amino methyl 2-methyl-5-((2R)-2-((((R)-1-(naphthalen-1-yl)ethyl)amino) methyl) chroman-4-yl)benzoate hydrochloride (Compound-3)

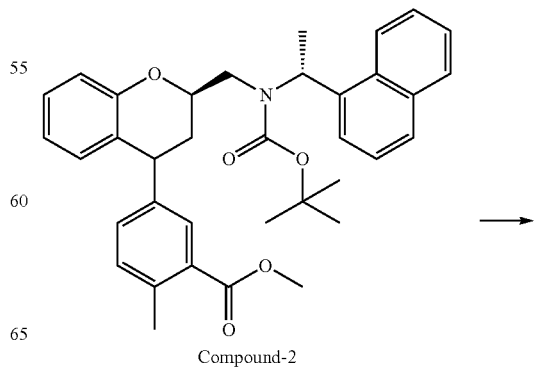

Compound-2

-continued

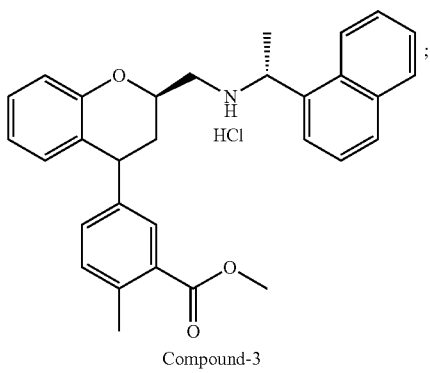

Compound-3 c) hydrolyzing the ester group of Compound-3 and isolating the pure diastereoisomer by using recrystallization technique to give 2-methyl-5-((2R,4S)-2-((((R)-1-(naphthalen-1-yl)ethyl)amino)methyl) chroman-4-yl) benzoic acid (Compound-4)

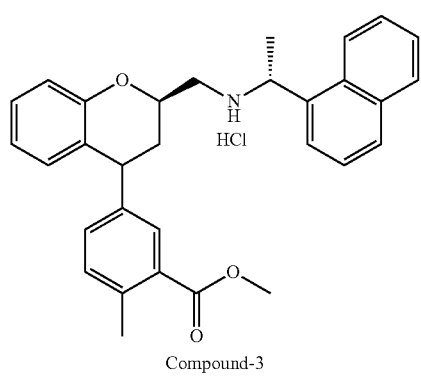

Compound-3

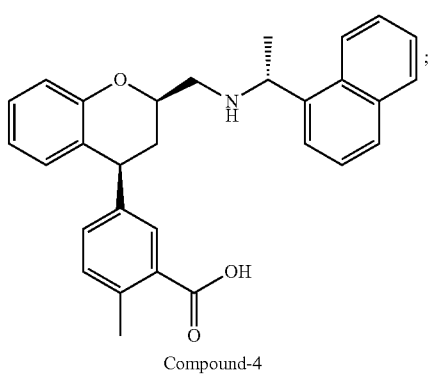

Compound-4 d) converting Compound-4 to its hydrochloride salt, 2-methyl-5-((2R,4S)-2-((((R)-1-(naphthalen-1-yl)ethyl)amino)methyl) chroman-4-yl)benzoic acid hydrochloride

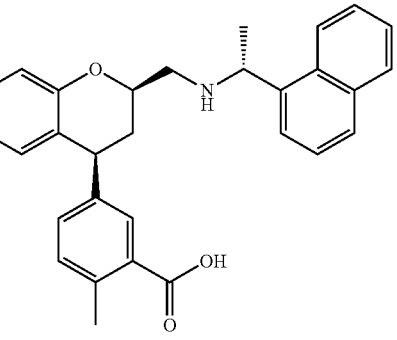

Compound-4

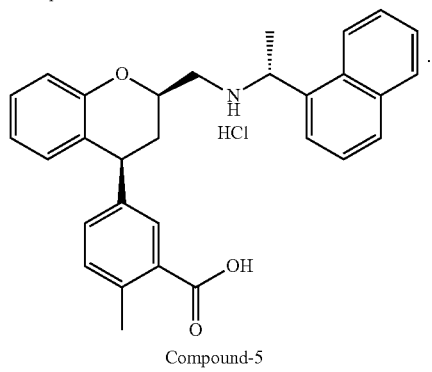

Compound-5

In some aspects, Compound-4 can be converted to a hydrobromide salt, a hydroiodide salt, a sulfate salt, a nitrate salt, a tosylate salt, or a carbonate salt.

In some aspects, the double bond in Compound-1 is reduced to give Compound-2, wherein the said reaction is carried-out by using ammonium formate (10 eq) and 5% Pd/C (50% wet and 10% w/w loading), 10% Pd/C or 2% Pd/C under heating at about 33° C. to about 34° C. in ethylacetate-methanol solvent system. This transfer hydrogenation can be performed with Pd—C catalyst using formate as a hydrogen source, for example, ammonium formate or sodium formate in an aqueous or organic solvent. The inventors have designed a synthesis route for Compound-A involving formate as the hydrogen source to enable the synthesis route to be safely scaled up without the need for exogenous hydrogen gas as the reducing agent. Avoiding the use of exogenous hydrogen gas also affords reduced infrastructure costs for scale-up, which would otherwise be required to minimize hazards associated with hydrogen gas explosions. The inventors have thus recognized that the synthesis routes described herein which do not involve the use of exogenous hydrogen gas yields significant benefits.

In some aspects, the reduction of the double bond in Compound-1 to give Compound-2 is carried out at a temperature between about 10° C. and about 50° C., more preferably at about 30° C. to about 33° C. The reaction can be conducted in any suitable solvent, which can include or exclude: halogenated hydrocarbons, $C_6$ to $C_{14}$ aromatic hydrocarbons, $C_1$ to $C_5$ alcohols, $C_2$ to $C_7$ esters, $C_4$ to $C_7$ ethers, $C_1$ to $C_5$ carboxylic acids, water, or suitable mixtures thereof. In some aspects, the reaction solvent can include or exclude: water, methanol, isopropyl alcohol, dichloromethane, toluene, ethyl acetate, diethyl ether, and a combination thereof.

In some aspects, Boc-deprotection reaction of Compound-2 is carried-out by using hydrochloric acid under reflux at about 63° C. in methanol. In some aspects, the concentration of hydrochloric acid is 6 N aqueous HCl. In some aspects, Boc-deprotection can occur using $AlCl_3$, trifluoroacetic acid in dichloromethane, or sequential treatment of trimethyl silyl iodide then methanol. In some aspects, the Boc deprotection ncan be performed in the presence of a cation scavenger. The cation scavenger can include or exclude anisole or thioanisole.

In some aspects, hydrolysis of Compound-3 is carried out by using sodium hydroxide under heating at about 55° C. in a methanol-tetrahydrofuran solvent system. In some aspects, hydrolysis can occur using any hydroxide base (e.g., lithium hydroxide, potassium hydroxide, cesium hydroxide), or lithium chloride followed by aqueous reaction with the resultant lithium carboxylate salt into the carboxylic acid.

In some aspects, isolation of diastereomerically pure Compound-4 from the crude hydrolysis product of Compound-3 is carried-out by a recrystallization technique using a solvent mixture of a protic polar solvent and an aprotic polar solvent. In some aspects, the protic polar solvent can include or exclude: ethanol, methanol, isopropanol, or a combination thereof. In some aspects, the aprotic polar solvent can include or exclude dichloromethane, dimethylformamide, tetrahydrofuran, or a combination thereof. In some aspects, the recrystallization method involves heating the reaction mixture in a solvent, for example, above 55° C. in a mixture of a solvent-nonsolvent, and allowing the solution to slowly cool to room temperature or below whereby seed crystals of the desired compound (e.g., Compound 4) preferentially crystallize while an undesired compound (e.g., Compound 3) essentially remains in solution. Capture of the isolated substantially pure product (e.g., Compound 4), optionally followed by wash with a pre-cooled solution of the solvent-nonsolvent solution, results in substantially purified Compound 4 free of substantially free of impurities.

In some aspects, isolation of diastereomerically pure Compound-4 from the crude hydrolysis product of Compound-3 is carried-out by a recrystallization technique using an ethanol: dichloromethane solvent mixture. In some aspects, the (v/v) ratio of ethanol to dichloromethane can range from 1:5 to 5:1.

In some aspects, conversion of Compound-4 to Compound-A is carried out by using acid neutralization with hydrochloric acid. In some aspects, the hydrochloric acid is 2 N aqueous HCl.

In some aspects, the invention provides a process for the preparation of methyl 5-((R)-2-(((tert-butoxycarbonyl)((R)-1-(naphthalen-1-yl)ethyl)amino)methyl)-2H-chromen-4-yl)-2-methylbenzoate (Compound-1), wherein the process comprises the steps:

a) reducing the amide group of (R)—N—((R)-1-(naphthalen-1-yl)ethyl)chroman-2-carboxamide (Compound-5) using sodium bis(2-methoxyethoxy)aluminium hydride (such as the sodium bis(2-methoxyethoxy)aluminium hydride known by the brand name Vitride™) in toluene followed by hydrochloride salt formation using concentrated HCl to give (R)—N—((R)-chroman-2-ylmethyl)-1-(naphthalen-1-yl)ethanamine hydrochloride (Compound-6)

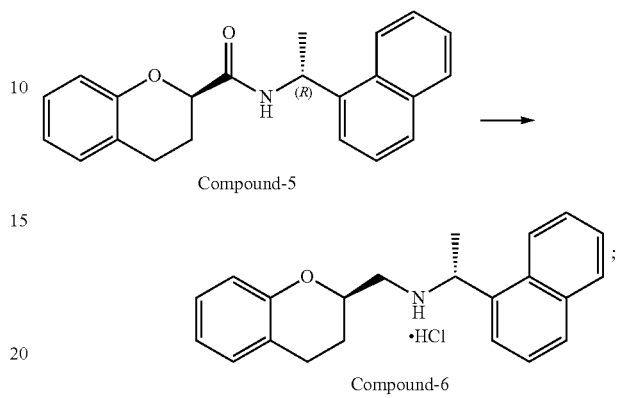

Compound-5

Compound-6 b) protecting the free amino group of Compound-6 using Boc anhydride (Di-tert-butyl dicarbonate) and tripotassium phosphate to give tert-butyl ((R)-chroman-2-ylmethyl)((R)-1-(naphthalen-1-yl)ethyl)carbamate (Compound-7)

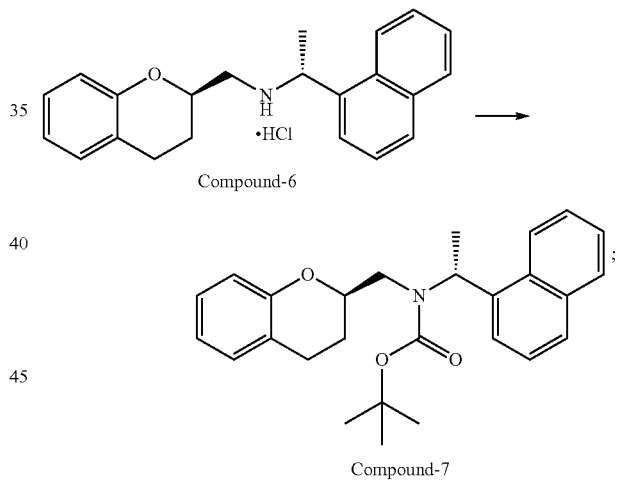

Compound-6

Compound-7 c) oxidizing Compound-7 using $KMnO_4$ and $MgSO_4$ to give tert-butyl ((R)-1-(naphthalen-1-yl)ethyl)(((R)-4-oxochroman-2-yl)methyl)carbamate (Compound-8)

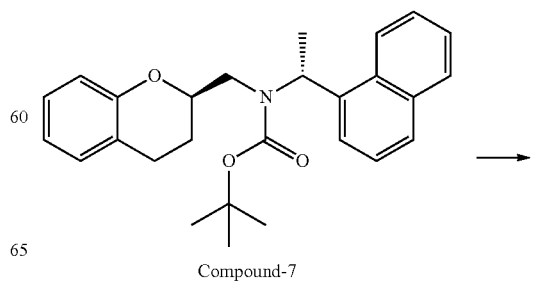

Compound-7

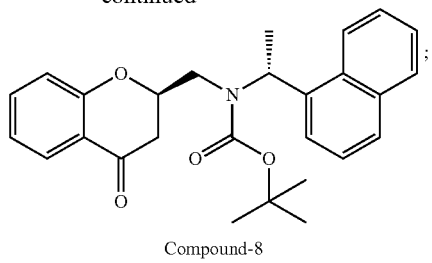

Compound-8 d) reacting Compound-8 with a triflating agent (which can include or exclude: N-phenyl-bis(trifluoromethanesulfonimide); trifluoromethanesulfonic anhydride; rifluoromethanesulfonyl chloride; 4-nitrophenyl trifluoromethanesulfonate or 1-(trifluoromethanesulfonyl) imidazole)) to give (R)-2-(((tert-butoxycarbonyl)((R)-1-(naphthalen-1-yl)ethyl)amino)methyl)-2H-chromen-4-yl trifluoromethanesulfonate (Compound-9)

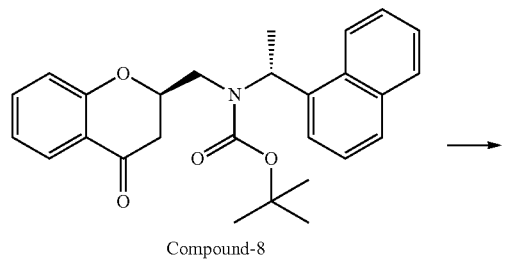

Compound-8

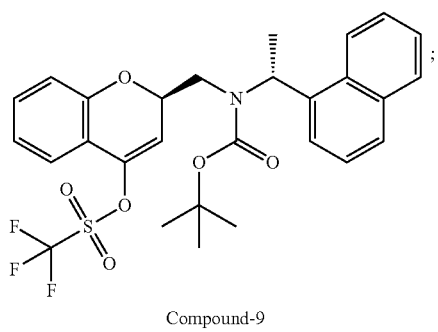

Compound-9 e) coupling Compound-9 with methyl 2-methyl-5-(4,4,5,5-tetramethyl-1,3,2-dioxaborolan-2-yl)benzoate in the presence of a palladium catalyst (which can include or exclude: palladium-tetrakis(triphenylphosphine); palladium(II)bis(triphenylphosphine) dichloride; palladium (0) bis(dibenzylideneacetone); palladium(II)bis(triphenylphosphine) diacetate; or [1,1'-bis(diphenylphosphino)ferrocene]dichloropalladium(II)) to give methyl-5-((R)-2-(((tert-butoxycarbonyl)((R)-1-(naphthalen-1-yl)ethyl)amino)methyl)-2H-chromen-4-yl)-2-methylbenzoate (Compound-1)

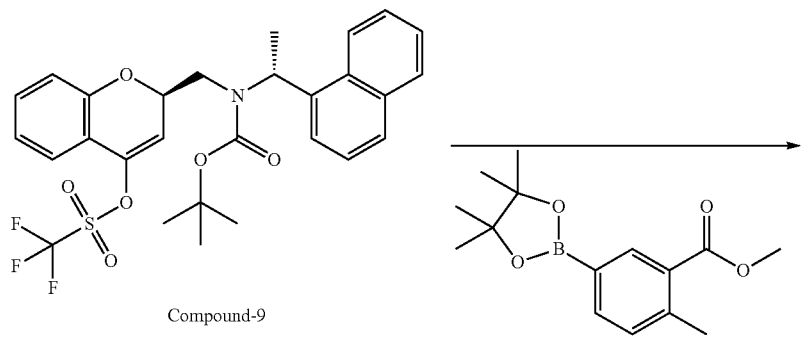

Compound-9

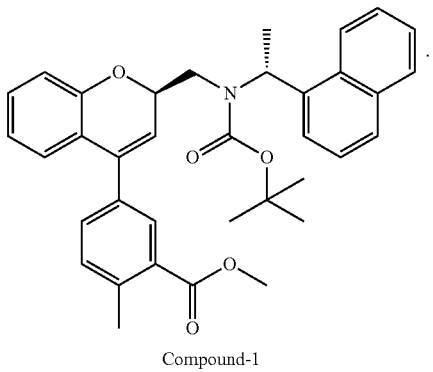

Compound-1

In some aspects, reduction of Compound-5 is carried out by using sodium bis(2-methoxyethoxy)aluminium hydride (such as the sodium bis(2-methoxyethoxy)aluminium hydride known by the brand name Vitride™) in toluene (70% w/w). Sodium bis(2-methoxyethoxy) aluminium hydride is a non-pyrophoric reducing agent.

BRIEF DESCRIPTION OF THE DRAWINGS

The drawings form part of the present specification and are included to further demonstrate certain aspects of the embodiments described herein. These embodiments may be better understood by reference to one or more of the following drawings in combination with the Detailed Description

DETAILED DESCRIPTION

Figure 1:
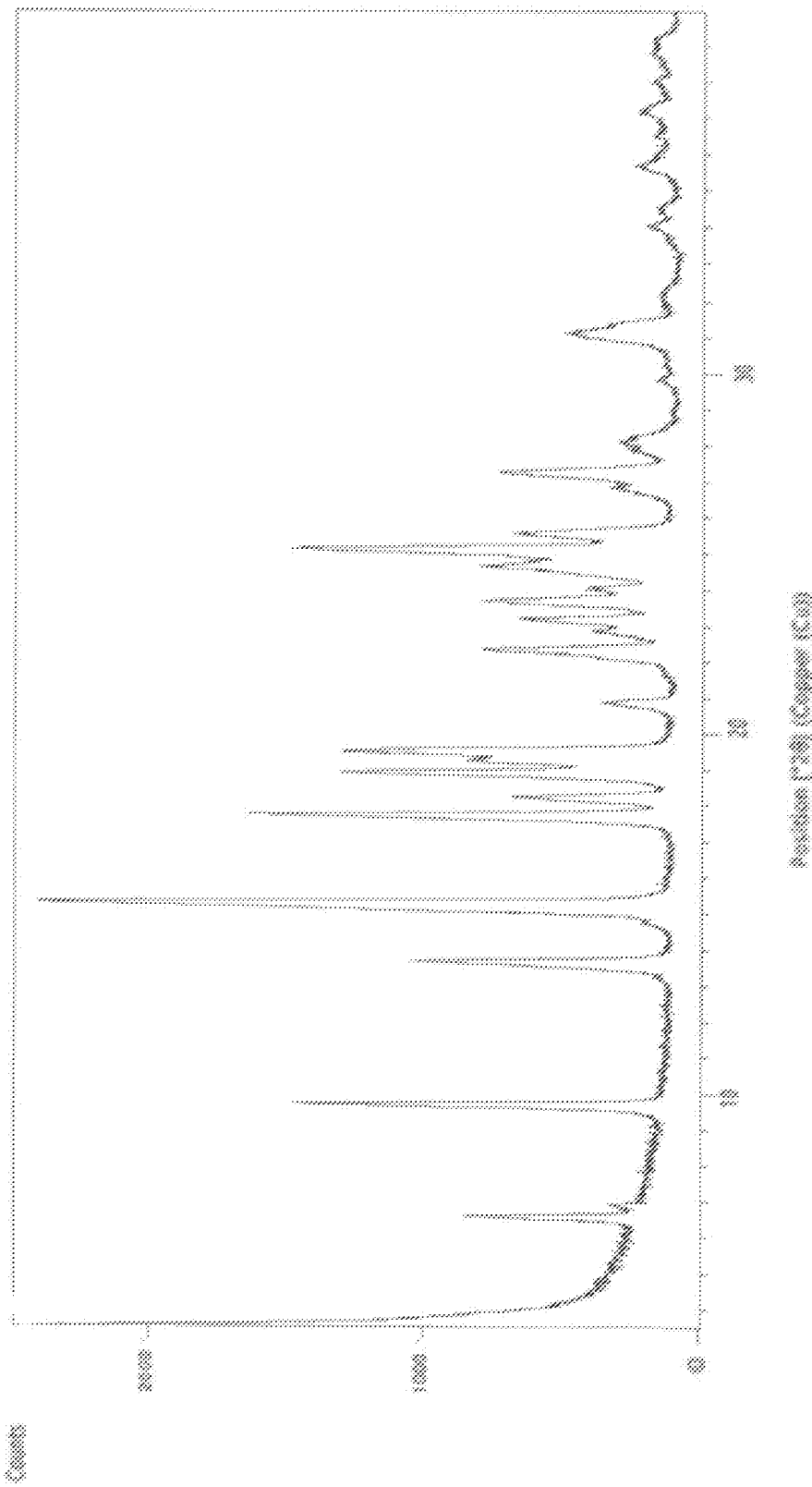
FIG. 1 is a powder X-ray diffraction profile of Compound-A made by a representative synthesis route of this disclosure (x-axis is the 2-theta coordinate)

It is to be understood that the processes, methods and/or systems herein are not limited to specific synthetic processes, methods or systems, specific components, or to particular compositions. It is also to be understood that the terminology used herein is for the purpose of describing particular embodiments only and is not intended to be limiting.

Definitions

General terms used in formula can be defined as follows; however, the meaning stated should not be interpreted as limiting the scope of the term per se.

As used herein, the recitation of a numerical range for a variable is intended to convey that the invention may be practiced with the variable equal to any of the values within that range. Thus, for a variable that is inherently discrete, the variable can be equal to any integer value of the numerical range, including the endpoints of the range. Similarly, for a variable, which is inherently continuous, the variable can be equal to any real value of the numerical range, including the endpoints of the range. As an example, a variable which is described as having values between 0 and 2, can be 0, 1 or 2 for variables which are inherently discrete, and can be 0.0, 0.1, 0.01, 0.001, or any other real value, for variables which are inherently continuous.

As used herein, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the term "about" is intended to qualify the numerical values which it modifies, denoting such a value as variable within a margin of error. When no particular margin of error, such as a standard deviation to a mean value, is recited, the term "about" means plus or minus 10% of the numerical value of the number with which it is being used. By way of example, "about 50%" means in the range of 45% to 55%.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol.

As used herein, the term "diastereomers" refers to stereoisomers which are not mirror images of each other. The term "Isomers" refers to compounds of having identical molecular formulae but differ in the nature or sequence of bonding of their atoms or in the arrangement of their atoms in space. Isomers that differ in the arrangement of their atoms in space are termed "stereoisomers". Diastereoisomers that are nonsuperimposable mirror images are termed "enantiomers" or sometimes "optical isomers". A carbon atom bonded to four nonidentical substituents is termed a "chiral center". A compound with one chiral center that has two enantiomeric forms of opposite chirality is termed a "racemic mixture". A compound that has more than one chiral center has 2n-1 enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

As used herein, the term "pharmaceutically acceptable" refers to that which is useful in preparing a pharmaceutical composition that is generally safe, non-toxic and neither biologically nor otherwise undesirable and includes that which is acceptable for veterinary use as well as human pharmaceutical use.

As used herein, the term "pharmaceutically acceptable salts" refers to salts of compounds of this disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, O-(4-hydroxybenzoyl)benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts that may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

As used herein, the term "pyrophoric" refers to a substance that ignites spontaneously in the presence of air or within 5 minutes after coming into contact with air. Common reducing agents are often pyrophoric, and include LiAlH4, NaH, diisobutyl aluminum hydride, metal hydrides, tributyl tin, borane complexes (e.g., $BH_3$-THF), hydrogen gas (with a catalyst), and the like. As used herein, a "non-pyrophoric" agent refers to a substance that does not ignite spontaneously in the presence of air or within 5 minutes after coming contact with air.

As used herein, the term "appropriate crystallization conditions" refers to conditions which are selected such that the desired compound of a mixture of compounds is crystallized, preferably, Compound 4 from a mixture of Compound 3 and Compound 4. Examples of solvent systems that may be used to perform this crystallization include, but are not limited to, alcohols and mixtures of alcohols with one or more co-solvents, such as, but not limited to tert-butyl methyl ether and dichloromethane. The ratio of ethanol to dichloromethane is selected such that the desired compound is crystallized. The ratio may range from about 5:1 to about 1:5 (v/v). The appropriate conditions may also include the addition of an acid. Examples of such acids include hydrochloric acid. Alternatively, other solvent systems may also be used, such as, combinations of a protic solvent and an aprotic solvent. In some embodiments, a seed crystal is added to catalyze the crystallization process while the solution is cooling. A seed crystal can include or exclude sodium sulfate, a crystalline form of the desired compound, or sodium chloride.

As used herein, the term "protic solvent" refers to a solvent that contains a dissociable $H^+$ or a group capable of forming hydrogen bonds (e.g., hydroxyl or amine group). Examples are water, methanol, ethanol, isopropanol, formic acid, hydrogen fluoride and ammonia. Preferred protic solvents include alcohols, such as methanol.

As used herein, the term "aprotic solvent" refers to a solvent that does not donate a hydrogen bond under normal reaction conditions for the selected reaction. Examples are HMPA, acetone, THF (tetrahydrofuran), diethyl ether, acetonitrile, DMF (dimethylformamide), DMSO (dimethyl sulfoxide), chloroform, and DCM (dichloromethane).

The compounds described herein may be prepared by synthetic organic chemistry processes or methods. Further, in the schemes described herein, where specific bases, acids, reagents, solvents, coupling agents, etc., are mentioned, it is understood that other bases, acids, reagents, solvents, coupling agents etc., unless otherwise specified, may also be used and are therefore included within the scope of the invention. Variations in reaction conditions, for example, temperature and/or duration of the reaction, which may be used as known in the art, are also within the scope of the invention. All the isomers of the compounds described in these schemes, unless otherwise specified, are also encompassed within the scope of this invention. The processes provided herein are as depicted in Scheme-1 and Scheme-2. Unless indicated otherwise, the temperatures at which a reaction of Scheme 1 or Scheme 2 is conducted is not critical. In certain embodiments, when a temperature is indicated in a reaction, the temperature may be varied from about plus or minus about 0.1° C., about 0.5° C., about 1° C., about 5° C., or about 10° C. Depending upon which solvent is employed in a particular reaction, the optimum temperature may vary. In conducting a reaction provided herein, neither the rate, nor the order, of addition of the reactants is critical unless otherwise indicated. Unless otherwise indicated, reactions are conducted at ambient atmospheric pressure. Unless otherwise indicated, the exact amount of reactants is not critical. In some embodiments, the amount of a reactant may be varied by about 10 mole % or about 10% by weight.

In some embodiments, this disclosure provides for synthetic routes to Compound-A which are economically scalable and therefore commercially manufacturable. The synthetic routes to Compound-A described herein do not involve column chromatography purification steps, which would otherwise lead to expensive operations to achieve commercial quantities of Compound-A. The inventors have surprisingly developed a synthetic route to Compound-A which, while involving additional steps beyond those described in WO2013/124828, actually results in a higher overall yield than the reference method because of the elimination of yield-losing column chromatography steps. The synthetic routes described herein have also been designed to eliminate the use of pyrophoric compounds, and hydrogen gas as a direct input, resulting in a safer manufacturable method of Compound-A. In some embodiments, sodium bis(2-methoxyethoxy)aluminium hydride (such as the sodium bis(2-methoxyethoxy)aluminium hydride known by the brand name Vitride™) is used as the reducing agent. Sodium bis(2-methoxyethoxy)aluminium hydride is a non-pyrophoric reducing agent that is otherwise equivalent in function to lithium aluminum hydride (lithium aluminum hydride is not used in the processes described herein). In some embodiments, an aqueous/organic formate salt (e.g., ammonium formate) is used as an indirect hydrogen source in the place of hydrogen gas for Pd—C catalyzed hydrogenations. Without being bound by theory, it is believed that the formate salt dissociates in solution to generate hydrogen, which then transiently bind to the Pd catalyst surface to serve as the hydrogenation source.

Provided herein is a process (as depicted in Scheme-1) for the preparation of Compound-A of the formula:

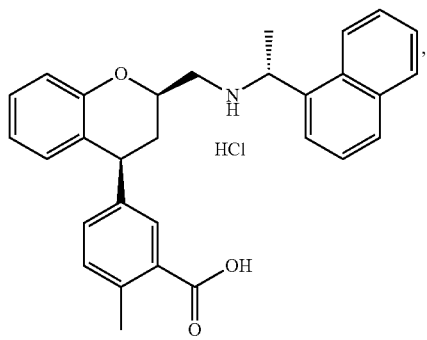

Compound-A wherein the process comprises:

1) reducing Compound-1 by using 5% Pd/C and ammonium formate under heating at about 33° C. to about 34° C. in a methanol-ethyl acetate solvent system to give Compound-2;

2) deprotecting the Boc-protected amine group of Compound-2, by refluxing the Compound-2 with 6 N HCl in methanol to give Compound-3;

3) hydrolyzing the ester group of Compound-3, by heating the Compound-3 at about 55° C. with 10 N NaOH in methanol-THF to give crude Compound-4, further the obtained crude compound was purified by recrystallization using ethanol:DCM (5:1 v/v) solvent system followed by recrystallization using isopropanol to give diastereomerically pure Compound-4;

4) converting the Compound-4 to its hydrochloride salt (Compound-A) using 2 N aqueous HCl.

Scheme-1

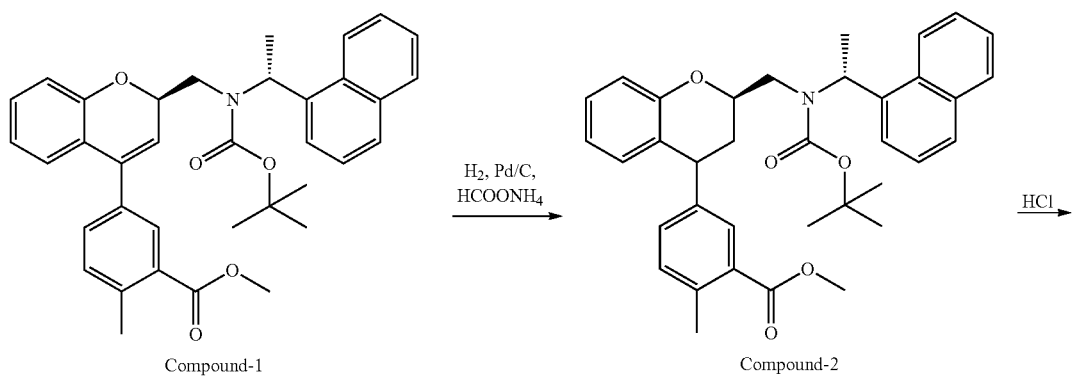

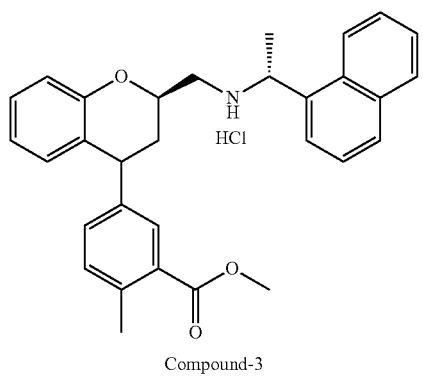

17

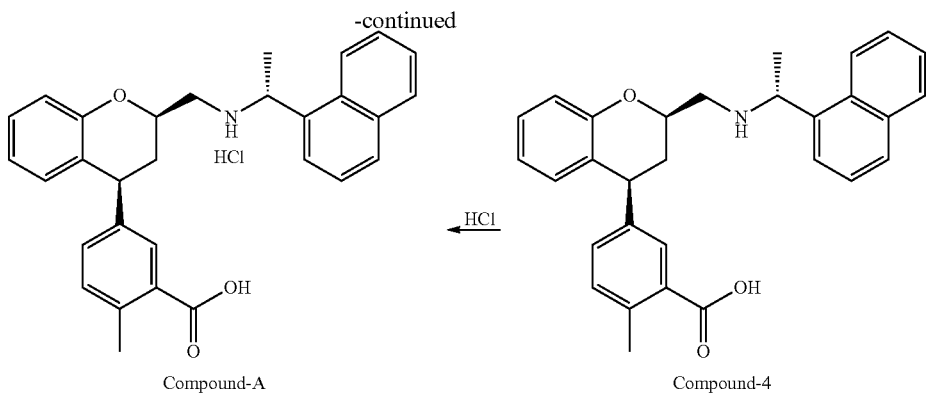

Compound-A

18

Compound-4

Provided herein is a process (as depicted in Scheme-1A) for the preparation of Compound-B of the formula:

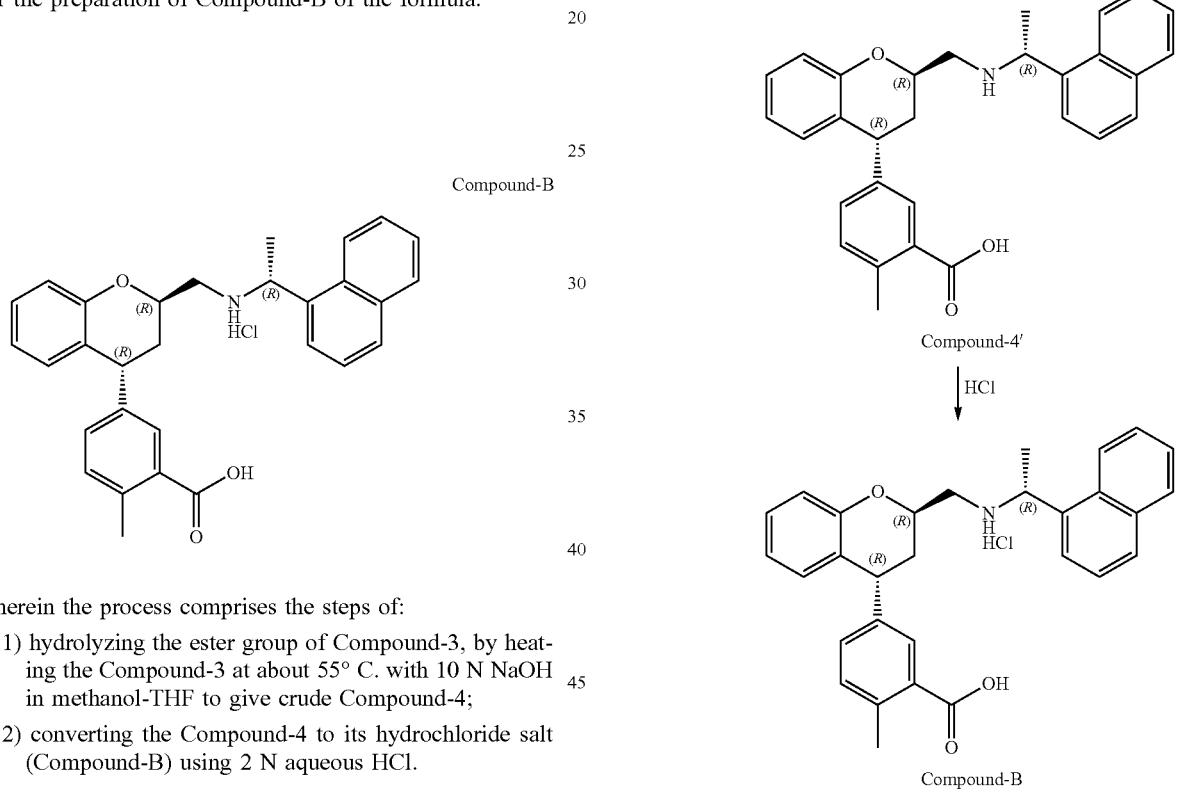

Compound-B wherein the process comprises the steps of:
1) hydrolyzing the ester group of Compound-3, by heating the Compound-3 at about 55° C. with 10 N NaOH in methanol-THF to give crude Compound-4;
2) converting the Compound-4 to its hydrochloride salt (Compound-B) using 2 N aqueous HCl.

Scheme-1A

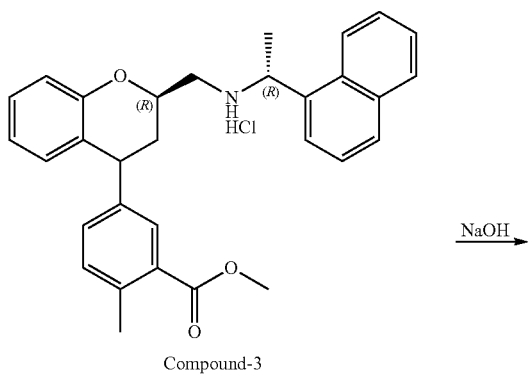

Compound-3

Compound-4′

Compound-B

Also provided herein is a process (as depicted in Scheme-2) for the preparation of Compound-1, which comprises:
1) reducing the Compound-5 by using sodium bis(2-methoxyethoxy)aluminium hydride (such as the sodium bis(2-methoxyethoxy)aluminium hydride known by the brand name Vitride™) in toluene (70% w/w) under heating conditions at about 85° C. in methanol-THF to give reduced product of Compound-5, which on treatment with concentrated HCl gives Compound-6;
2) protecting the free amino group of Compound-6 by using Boc anhydride in presence of tripotassium phosphate in a DCM-water solvent system, to give Compound-7;
3) oxidizing Compound-7 using potassium permanganate and magnesium sulphate in acetone-water solvent system to give Compound-8;

4) reacting Compound-8 with N-phenyl-bis(trifluoromethanesulfonimide) (PhNTf$_2$) in the presence of potassium bis(trimethylsilyl)amide (KHMDS) and hexamethylphosphoramide (HMPA) at −83° C. in THF to give Compound-9; 5) coupling of Compound-9 with methyl 2-methyl-5-(4,4,5,5-tetramethyl-1,3,2-dioxaborolan-2-yl)benzoate in presence of tetrakis(triphenylphosphine) palladium(0) and tripotassium phosphate in THF, under reflux conditions to give Compound-1.

Scheme-2
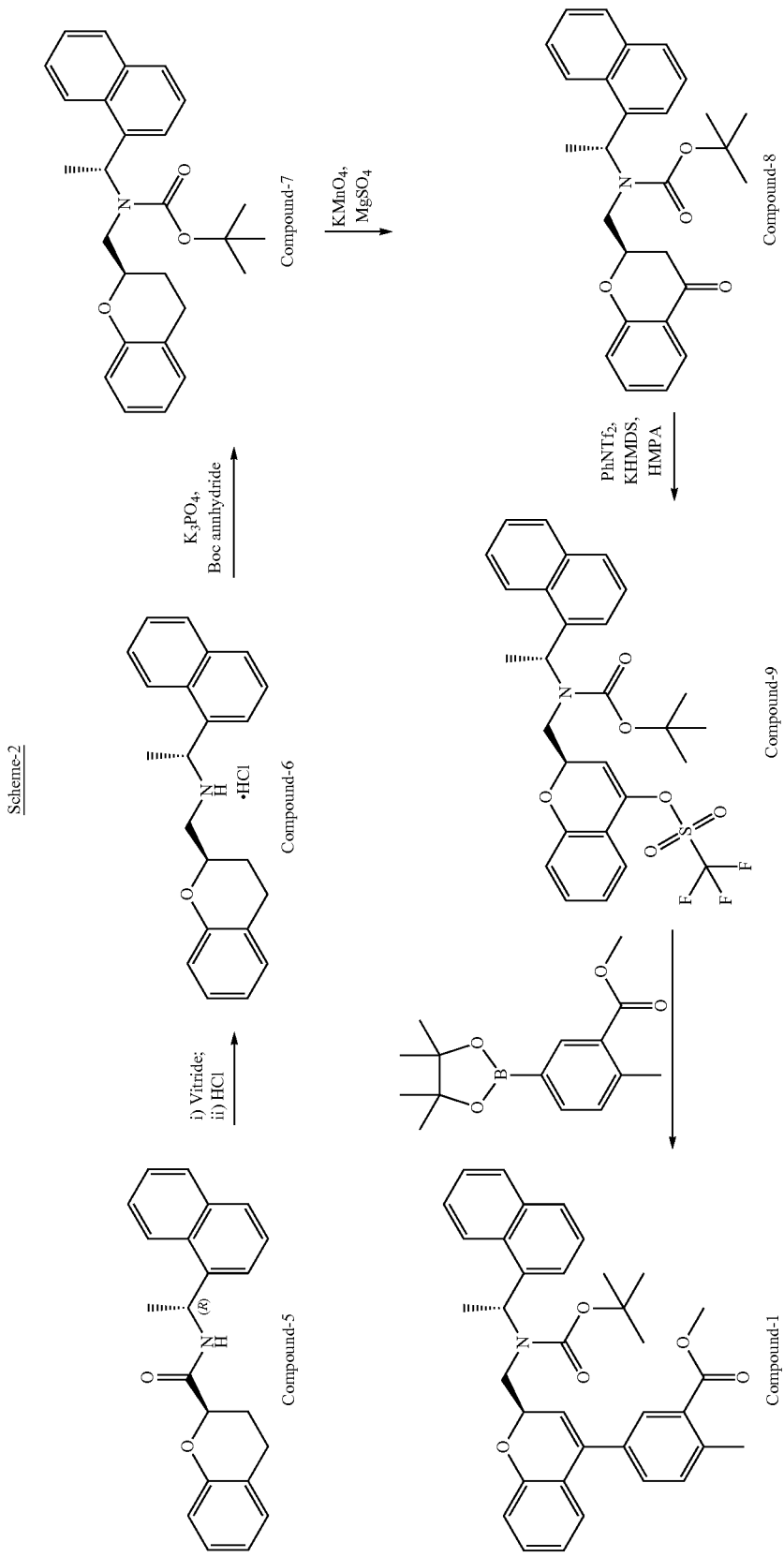

Manufacture and Purity

The compounds of this disclosure, including Compound-4 and Compound-A, may be prepared as previously described. The compounds of this disclosure can be manufactured at significantly large scale with relative safety because no gaseous exogenous hydrogenation steps are involved. In some embodiments, the compounds of this disclosure for large-scale manufacturing purposes can be made at 1 kg, 10 kg, 100 kg, 1000 kg, 10000 kg, or 100000 kg scale of final product, or any scale between the aforementioned scales.

In some embodiments, the compounds of this invention are substantially pure. By substantially pure is meant that the compounds comprise less than about 5%, 4%, 3%, 2%, 1%, 0.9%, 0.8%, 0.7%, 0.6%, 0.5%, 0.4%, 0.3%, 0.2%, 0.1%, and preferably less than about 0.1%, of any impurity. In some embodiments the total impurities, including unreacted reactants or side products (e.g., Compound 3 after the reaction to synthesize Compound 4), will be not more than 0.1-5%. The amounts of impurities can be measured using HPLC (including RP-HPLC, HPLC-MS, HPLC-MS/MS, HPLC-UV, and IEX) per methods understood in the art.

EXAMPLES

The invention is illustrated in more details by the examples described herein, but the invention should not be construed to be limited thereto.

Compounds of this invention can be made by the methods and processes depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

Unless specified to the contrary, the reactions described herein take place at atmospheric pressure over a temperature range from about −78° C. to about 150° C., more preferably from about 0° C. to about 125° C., and most preferably at about 10° C. to about 40° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples, see T. W. Greene and P. G. M. Wuts in "Protective Groups in Organic Chemistry" John Wiley and Sons, 1999.

Example 1. Synthesis, Purification, and Characterization of Compound-A

Step-1: (R)—N—((R)-chroman-2-ylmethyl)-1-(naphthalen-1-yl)ethanamine: hydrochloride

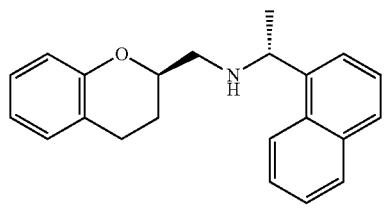 [SMILES: C[C@@H](NC[C@H]1CCc2ccccc2O1)c1cccc2ccccc12]

To a solution of (R)—N—((R)-1-(naphthalen-1-yl)ethyl) chroman-2-carboxamide (1.0 eq) in 2-MeTHF (5.0 v) under nitrogen, was added sodium bis(2-methoxyethoxy)aluminium hydride (such as the sodium bis(2-methoxyethoxy) aluminium hydride known by the brand name Vitride™) in toluene (70% w/w) (2.6 eq) over a period of 1 h at 5±5° C. The above reaction mixture was stirred for 1 h at ambient temperature, and further heated to 85±5° C. for 6 h. The reaction mass was cooled to 10±5° C., and excess of sodium bis(2-methoxyethoxy)aluminium hydride (such as the sodium bis(2-methoxyethoxy)aluminium hydride known by the brand name Vitride™) was quenched using ethyl acetate (2.0 eq). This was then stirred for 30 min. To the above solution was added purified water (1.0 eq) and stirred for 1 h. 5 N aqueous solution of NaOH (5.0 v) was added to the above reaction mass at 20±5° C. and stirred for additional 30 min. Organic phase was separated, and aqueous phase was extracted using MTBE (4.0 v), and once again with MTBE (2.0 v). Combined organic phase was washed with saturated solution of brine (5.0 v). The organic phase was separated, and evaporated under vacuum to ~5-7 v at 40±5° C. Concentrated HCl (1.5 eq) was added to the above reaction mixture at 10±5° C. and stirred for 2 h. Solid precipitated was filtered, washed with purified water (0.5 v) and MTBE (0.5 v). The wet cake was then dried under vacuum oven at 40±5° C. for 10 h to give (R)—N—((R)-chroman-2-ylmethyl)-1-(naphthalen-1-yl) ethanamine hydrochloride.

Yield: 92.9%

Mass:318.0 [MH+]

$^1$H NMR (300 MHz, DMSO-d6) δ: 10.21-9.64 (bs, 2H), 8.29-8.26 (d, J=8.1 Hz, 1H), 8.10-7.98 (m, 3H), 7.66-7.58 (m, 3H), 7.11-7.06 (m, 2H), 6.86-6.76 (m, 2H), 5.45 (bs, 1H), 4.49-4.46 (m, 1H), 3.34-3.17 (m, 2H), 2.86-2.66 (m, 2H), 2.06-2.00 (m, 1H), 1.76-1.74 (d, J=6.6 Hz, 3H), 1.70-1.57 (m, 1H).

Compound-6 can be isolated as the free base with following procedure: To a solution of (R)—N—((R)-1-(naphthalen-1-yl)ethyl)chroman-2-carboxamide (1.0 eq) in 2-MeTHF (5.0 v) under nitrogen, was added sodium bis(2-methoxyethoxy)aluminium hydride (such as the sodium bis(2-methoxyethoxy)aluminium hydride known by the brand name Vitride™) in toluene (70% w/w) (2.6 eq) over a period of 1 h at 5±5° C. The above reaction mixture was stirred for 1 h at ambient temperature, and further heated to 85±5° C. for 6 h. The reaction mass was cooled to 10±5° C., and excess of sodium bis(2-methoxyethoxy)aluminium hydride (such as the sodium bis(2-methoxyethoxy)aluminium hydride known by the brand name Vitride™) was quenched using ethyl acetate (2.0 eq). This was then stirred for 30 min. To the above solution was added purified water (1.0 eq) and stirred for 1 h. 5 N aqueous solution of NaOH (5.0 v) was added to the above reaction mass at 20±5° C. and stirred for additional 30 min. Organic phase was separated, and aqueous phase was extracted using MTBE (4.0 v), and once again with MTBE (2.0 v). Combined organic phase was washed with saturated solution of brine (5.0 v). The organic phase was separated, and evaporated under vacuum to ~5-7 v at 40±5° C. The above mass was swabbed with ethanol (2 v) and fresh ethanol (3 v) added to get a clear solution at 40±5° C. It was cool to 25-30° C. and stirred for 1 h. Then it was cool to 0-5° C., solid precipitated filtered, washed with ice-cold ethanol (1 v) and the wet solid was then dried under vacuum oven at 50±5° C. for 14 h to give (R)—N—((R)-chroman-2-ylmethyl)-1-(naphthalen-1-yl) ethanamine.

Yield: 75.98%

Mass: 318.46 [MH+]

$^1$H NMR (400 MHz, DMSO-$d_6$) δ: 8.34-8.27 (m, 1H), 7.93 (dd, J=7.9, 1.7 Hz, 1H), 7.80 (d, J=8.1 Hz, 1H), 7.73 (dd, J=7.3, 1.2 Hz, 1H), 7.58-7.46 (m, 3H), 7.07-6.99 (m, 2H), 6.78 (td, J=7.4, 1.2 Hz, 1H), 6.71 (dd, J=8.5, 1.2 Hz, 1H), 4.73-4.58 (m, 1H), 4.09 (dtd, J=9.9, 6.0, 2.2 Hz, 1H), 2.77 (ddt, J=19.0, 14.2, 6.9 Hz, 2H), 2.70-2.54 (m, 2H), 2.35 (s, 1H), 2.11-1.97 (m, 1H), 1.61 (dddd, J=13.5, 11.1, 9.9, 5.5 Hz, 1H), 1.42 (d, J=6.5 Hz, 3H).

Step-2: tert-butyl ((R)-chroman-2-ylmethyl)((R)-1-(naphthalen-1-yl)ethyl)carbamate

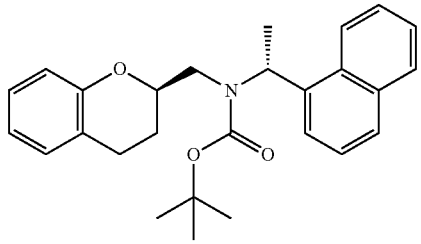 [SMILES: C[C@H](c1cccc2ccccc12)N(C[C@H]1CCc2ccccc2O1)C(=O)OC(C)(C)C]

To a solution of (R)—N—((R)-chroman-2-ylmethyl)-1-(naphthalen-1-yl)ethanamine (1.0 eq) in DCM (4.0 v) was added a solution of K$_3$PO$_4$ (1.5 eq) in purified water (3.0 v) at 15±5° C. To above solution was added (Boc)$_2$O (1.1 eq) dissolved in DCM (1.0 v) at the same temperature. The above solution was stirred at 25±5° C. for a period of 18 h. Organic phase was separated, evaporated under vacuum to ~2.0 v. DCM (dichloromethane) was switched for ethanol (1.0 v). In to this solution, fresh ethanol (3 v) was added and heated to 50±5° C. gave clear solution, then it was cool to ambient temperature and stirred for 1 h at 0±5° C. The product precipitated was filtered and washed with ice-cold ethanol (1 v). The wet solid was dried in vacuum tray dryier for 16 h to afford the product tert-butyl ((R)-chroman-2-ylmethyl)((R)-1-(naphthalen-1-yl)ethyl)carbamate.

Yield: 98%

Mass: 440.13[M+Na]

$^1$H NMR (400 MHz, DMSO-$d_6$) δ: 8.06 (bs, 1H), 7.96 (dd, J=7.7, 1.8 Hz, 1H), 7.89 (d, J=8.2 Hz, 1H), 7.69 (d, J=7.1 Hz, 1H), 7.62-7.47 (m, 3H), 6.96-6.85 (m, 1H), 6.82 (dd, J=7.6, 1.6 Hz, 1H), 6.66 (td, J=7.4, 1.3 Hz, 1H), 6.21 (s, 1H), 3.18 (s, 2H), 2.65 (s, 2H), 2.38 (d, J=16.7 Hz, 1H), 1.81 (s, 1H), 1.64 (d, J=6.8 Hz, 3H), 1.53-1.43 (m, 9H), 1.35-1.10 (m, 2H).

Step-3: tert-butyl ((R)-1-(naphthalen-1-yl)ethyl) (((R)-4-oxochroman-2-yl)methyl)carbamate

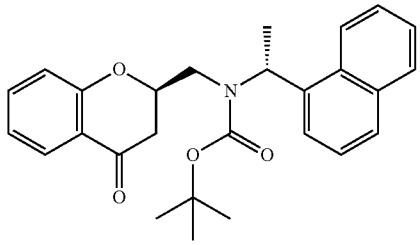 [SMILES: C[C@H](c1cccc2ccccc12)N(C[C@H]1CC(=O)c2ccccc2O1)C(=O)OC(C)(C)C]

A solution of tert-butyl ((R)-chroman-2-ylmethyl)((R)-1-(naphthalen-1-yl)ethyl)carbamate (1.0 eq) in acetone (25.0 v) and purified water (6.0 v) was warmed to 42±5° C. Into this solution was added MgSO$_4$ (3.5 eq) followed by KMnO$_4$ (7.0 eq) portion wise over a period of ~3 h. The above reaction mass was stirred for 8-16 h at the same temperature. Reaction mass was cooled to 15±5° C. Saturated aqueous Na$_2$SO$_3$ solution (0.84 w/w) was added at the same temperature. This was allowed to stir for 30 min. Kieselguhr (1.0 w/w) was charged to the above reaction mass and stirred for 1 h at 35±5° C. Centrifuge the above and the filter cake was added to reactor containing acetone (7.85 w/w) and refluxed for 3 h. The above reaction mass was filtered and was concentrated to ~6.0 v. Into this was added a saturated solution of brine (1.20 w/w). The product was extracted with ethyl acetate (10.0 v×2). Organic layer separated and given a brine wash (2.4 w/w). Organic phase separated, evaporated under vacuum to ~3.0 v. THF (3.0 v) was added to the above and concentrated to afford tert-butyl ((R)-1-(naphthalen-1-yl)ethyl)(((R)-4-oxochroman-2-yl) methyl)carbamate.

Yield: 99%

Mass: 454.12[M+Na]

$^1$H NMR (400 MHz, DMSO-$d_6$) δ: 8.10-8.00 (m, 1H), 7.97 (dd, J=7.9, 1.6 Hz, 1H), 7.90 (d, J=8.1 Hz, 1H), 7.69 (d, J=7.2 Hz, 1H), 7.60-7.50 (m, 4H), 7.37 (ddd, J=8.7, 7.2, 1.8 Hz, 1H), 6.92 (td, J=7.6, 1.0 Hz, 1H), 6.18 (d, J=8.3 Hz, 1H), 3.66 (tt, J=8.1, 4.9 Hz, 1H), 3.40-3.21 (m, 3H), 2.44 (d, J=14.4 Hz, 1H), 2.25 (dd, J=17.0, 3.2 Hz, 1H), 1.64 (d, J=6.8 Hz, 3H), 1.48 (d, J=12.2 Hz, 9H).

Step-4: (R)-2-(((tert-butoxycarbonyl)((R)-1-(naphthalen-1-yl)ethyl)amino)methyl)-2H-chromen-4-yl trifluoromethanesulfonate

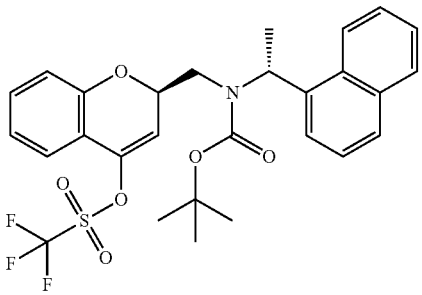 [SMILES: C[C@H](c1cccc2ccccc12)N(C[C@H]1C=C(OS(=O)(=O)C(F)(F)F)c2ccccc2O1)C(=O)OC(C)(C)C]

To a solution of tert-butyl ((R)-1-(naphthalen-1-yl)ethyl) (((R)-4-oxochroman-2-yl)methyl)carbamate (1.0 eq) in THF (7.0 v) was added HMPA (0.0015 v) under nitrogen. Potassium bis(trimethylsilyl)amide (KHMDS) solution (1M in THF) (1.5 eq) was added drop wise to the above solution at −83±5° C. over a period of 1 h 30 min. The above reaction mass was allowed to stir for 45 min at −83±5° C. A solution of N-Phenyl-bis(trifluoromethanesulfonimide) (PhNTf$_2$) (1.5 eq) in THF (4.0 v) was added drop wise at same temperature over a period of 3 h 10 min. this was stirred for further 30 min. Reaction was quenched using purified water (1.5 v) at −20±10° C. to get (R)-2-(((tert-butoxycarbonyl) ((R)-1-(naphthalen-1-yl)ethyl)amino)methyl)-2H-chromen-4-yl trifluoromethanesulfonate and used as such for the next step.

Alternate isolation procedure: Upon completion of reaction, the mass was quenched with purified water (1.5 v) at −20±10° C. THF was concentrated, and then product extracted with n-hexanes (5 v×3 time), combined extraction washed with water (5 v), and concentrated to get (R)-2-(((tert-butoxycarbonyl)((R)-1-(naphthalen-1-yl)ethyl) amino)methyl)-2H-chromen-4-yl trifluoromethanesulfonate.

Yield: 84%

Mass: 586.0[M+Na]

$^1$H NMR (400 MHz, DMSO-d$_6$) δ: 8.00 (dt, J=6.9, 3.5 Hz, 2H), 7.97-7.88 (m, 1H), 7.68 (s, 1H), 7.57 (ddd, J=8.7, 6.9, 3.0 Hz, 3H), 7.22 (t, J=7.7 Hz, 1H), 7.05 (dd, J=7.7, 1.6 Hz, 1H), 6.96 (td, J=7.6, 1.1 Hz, 1H), 6.45 (s, 1H), 6.09 (s, 1H), 5.30 (s, 1H), 3.95 (s, 1H), 1.63 (d, J=6.9 Hz, 3H), 1.39 (s, 9H), 1.24 (s, 2H).

Step-5: methyl5-((R)-2-(((tert-butoxycarbonyl)((R)-1-(naphthalen-1-yl)ethyl)amino)methyl)-2H-chromen-4-yl)-2-methylbenzoate

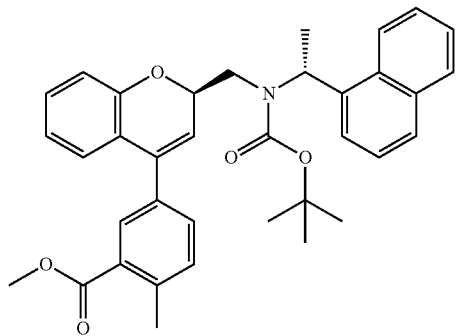 [SMILES: COC(=O)c1cc(C2=C[C@H](CN(C(=O)OC(C)(C)C)[C@H](C)c3cccc4ccccc34)Oc3ccccc32)ccc1C]

(R)-2-(((tert-butoxycarbonyl)((R)-1-(naphthalen-1-yl) ethyl)amino)methyl)-2H-chromen-4-yl trifluoromethanesulfonate in THF (1.0 eq) was added to the reactor under nitrogen. To the above solution were added methyl 2-methyl-5-(4,4,5,5-tetramethyl-1,3,2-dioxaborolan-2-yl) benzoate (0.95 eq) and K$_3$PO$_4$ (1.5 eq). Pd(PPh$_3$)$_4$(1.2 mol %) was added to the above solution under nitrogen at ambient temperature. Reaction mixture was heated to reflux temperature for 12-18 h. The reaction mass cooled to ambient temperature and into that was added celite (1 w/w), n-heptane (3.0 v) and water (1.0 v). The above reaction mass was filtered, layer separated and the aqueous phase was further extracted with MTBE (2.0 v).

To the combined organic phase were added activated Carbon (0.2 w/w), silica gel (1.0 w/w) and celite (1.0 w/w). The above mixture was stirred for 3 h at ambient temperature. The above mixture was filtered and reaction mass evaporated under vacuum to ~2 v. Isopropyl alcohol (2.0 v) was added to the above reaction mass and evaporated to ~2.0 v. This co distillation process was repeated once again. The above mass was cooled to 5±5° C. and stirred for 4-8 h at the same temperature and filtered to give methyl5-((R)-2-(((tert-butoxycarbonyl)((R)-1-(naphthalen-1-yl)ethyl)amino) methyl)-2H-chromen-4-yl)-2-methylbenzoate as a wet cake.

The above cake was stirred in Isopropyl alcohol (2.0 v) and heated to 68±5° C. to give a clear solution. This was then cooled to 15±5° C. and stirred for 16 h at the same temperature. Solid precipitated was filtered and the solids washed with Isopropyl alcohol (0.5 v). The above solid was dried under vacuum at 40±5° C. until LOD≤0.5%.

The above solid was added to the reactor containing ethyl acetate (3.15 v). The resulting solution was filtered through micro porous filter. The ethyl acetate layer was washed with purified water (1.5 w/w) for a period of 10 min. The organic phase was separated and washed again with purified water (1.5 w/w). Organic layer was separated and evaporated under vacuum to ~1.5-2 v at 40±5° C. The residue was codistilled with Isopropyl alcohol (or ethanol) (1.57 v) twice to ~1.5-2 v. Purified water (3.0 w/w) was added to the above solution. Isopropyl alcohol was removed by evaporation under vacuum to ~3.5-4 v at 40±5° C. Solid precipitated was filtered and washed with water (0.5 v). The solid thus obtained was dried under vacuum oven at 45±5° C. until LOD≤0.5% to give methyl5-((R)-2-(((tert-butoxycarbonyl) ((R)-1-(naphthalen-1-yl)ethyl)amino)methyl)-2H-chromen-4-yl)-2-methylbenzoate.

Yield: 56.81%

Mass: 586.44 [M+Na]

$^1$H NMR (400 MHz, DMSO-d$_6$) δ: 8.08 (d, J=8.0 Hz, 1H), 7.97 (dd, J=8.1, 1.4 Hz, 1H), 7.91 (d, J=8.2 Hz, 1H), 7.68 (d, J=7.2 Hz, 1H), 7.65-7.49 (m, 4H), 7.35 (d, J=7.9 Hz, 1H), 7.21 (s, 1H), 7.10-7.02 (m, 1H), 6.81-6.69 (m, 2H), 6.38 (bs, 1H), 6.11 (bs, 1H), 5.19 (bs, 1H), 3.85 (s, 3H), 3.75 (bs, 1H), 3.31 (m, 1H), 2.53 (s, 3H), 1.65 (d, J=6.8 Hz, 3H), 1.50 (bs, 1H), 1.32 (bs, 9H).

Alternate procedure: To the above solution of (R)-2-(((tert-butoxycarbonyl)((R)-1-(naphthalen-1-yl)ethyl) amino)methyl)-2H-chromen-4-yl trifluoromethanesulfonate (110 g, 195 mmol) in a mixture of THF (Volume: 500 ml, Ratio: 2.000) andWater (Volume: 250 ml, Ratio: 1.000) was added methyl 2-methyl-5-(4,4,5,5-tetramethyl-1,3,2-dioxaborolan-2-yl)benzoate (51.2 g, 185 mmol), potassium phosphate tribasic (91 g, 429 mmol) and Tetrakis (1.128 g, 0.976 mmol) sequentially under nitrogen. The mixture was heated to reflux for 18 h. Progress of the reaction was monitored by HPLC. After complete consumption of SM, the mass was filtered through celite pad and concentrated under reduced pressure. The residue was diluted with water and product extracted with n-hexanes (5 v×3 time), combined extraction washed with water (5 v) and concentrated under reduced pressure. The above residue was codistilled with ethanol (2 v), then fresh ethanol (4 v) was added and the resulting mixture was warmed to get clear solution. It was cool to room temperature and stirred for 18 h. The mass was cool to 0±5° C. with stirring for 1 h, product thus crystallized was filtered, and solid washed with ice-cold ethanol (1 v). The solid thus obtained was dried under vacuum oven at 45±5° C. until LOD≤0.5% to give methyl5-((R)-2-(((tert-butoxycarbonyl)((R)-1-(naphthalen-1-yl)ethyl)amino)methyl)-2H-chromen-4-yl)-2-methylbenzoate.

Yield: 82%

Mass: 586.44 [M+Na]

$^1$H NMR (400 MHz, DMSO-d$_6$) δ: 8.08 (d, J=8.0 Hz, 1H), 7.97 (dd, J=8.1, 1.4 Hz, 1H), 7.91 (d, J=8.2 Hz, 1H), 7.68 (d,

J=7.2 Hz, 1H), 7.65-7.49 (m, 4H), 7.35 (d, J=7.9 Hz, 1H), 7.21 (s, 1H), 7.10-7.02 (m, 1H), 6.81-6.69 (m, 2H), 6.38 (bs, 1H), 6.11 (bs, 1H), 5.19 (bs, 1H), 3.85 (s, 3H), 3.75 (bs, 1H), 3.31 (m, 1H), 2.53 (s, 3H), 1.65 (d, J=6.8 Hz, 3H), 1.50 (bs, 1H), 1.32 (bs, 9H).

Step-6: Methyl 5-((2R)-2-(((tert-butoxycarbonyl)((R)-1-(naphthalen-1-yl)ethyl)amino) methyl) chroman-4-yl)-2-methylbenzoate

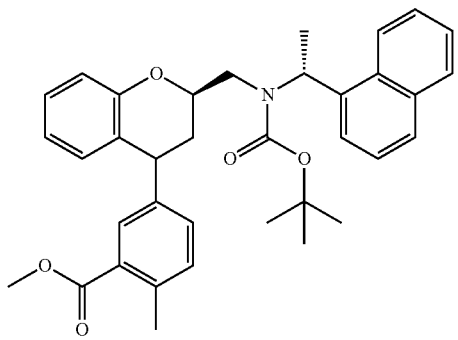

Ammonium formate (10.0 eq) was dissolved in methanol and, heated to 33-34° C. (6.0 v) giving a clear solution. Methyl5-((R)-2-(((tert-butoxycarbonyl)((R)-1-(naphthalen-1-yl)ethyl)amino)methyl)-2H-chromen-4-yl)-2-methylbenzoate (1.0 eq) was dissolved in ethyl acetate (3.0 v) and heated to 33-34° C., and 5% Pd/C 50% wet (10% w/w g) was added. Ammonium formate solution was then added with an addition funnel over a period of 6 h to the above suspension. The reaction mixture was heated at 33-34° C. for 2 h 30 min. The reaction mixture was cooled to 20° C. over a period of 4 h, and was allowed to stir for 9 hours at 20° C. Catalyst was filtered off through a GF/F glass microfiber filter and washed with methanol (1.0 v), then with ethyl acetate (2.0 v). The solution was successively concentrated at 250 mbar and diluted with ethyl acetate, in order to reach a 25/75 methanol/ethyl acetate molar ratio (NMR). To the white suspension thus obtained was added ethyl acetate (4.0 v) followed by water (8.0 v), allowing an easy separation of the two homogeneous layers. The organic layer was washed with the water (8.0 v), then successively concentrated at 250 mbar and diluted with methanol in order to remove ethyl acetate (NMR). Intermediate methyl 5-((2R)-2-(((tert-butoxycarbonyl)((R)-1-(naphthalen-1-yl)ethyl)amino) methyl) chroman-4-yl)-2-methylbenzoate was isolated as a methanol solution (~3.0 v) which was ready for use in the next step of the synthesis.

Yield: 100%

Mass: 588.25 [M+Na]

¹H NMR (400 MHz, DMSO-d₆) δ: 8.05 (dd, J=8.1, 1.5 Hz, 2H), 7.94 (d, J=8.2 Hz, 1H), 7.72 (d, J=7.1 Hz, 1H), 7.69-7.48 (m, 3H), 7.34 (d, J=2.0 Hz, 1H), 7.24 (d, J=7.9 Hz, 1H), 6.98 (dd, J=7.8, 2.0 Hz, 1H), 6.92 (t, J=7.3 Hz, 1H), 6.59 (td, J=7.5, 1.3 Hz, 1H), 6.33 (s, 1H), 6.27 (d, J=7.7 Hz, 1H), 6.14 (s, 1H), 3.83 (s, 3H), 3.21 (dd, J=14.4, 5.9 Hz, 2H), 2.48 (s, 3H), 1.66 (s, 3H), 1.48 (bs, 2H), 1.37 (bs, 9H), 1.24 (s, 2H).

Step-7: methyl 2-methyl-5-((2R)-2-((((R)-1-(naphthalen-1-yl)ethyl)amino) methyl) chroman-4-yl) benzoate hydrochloride

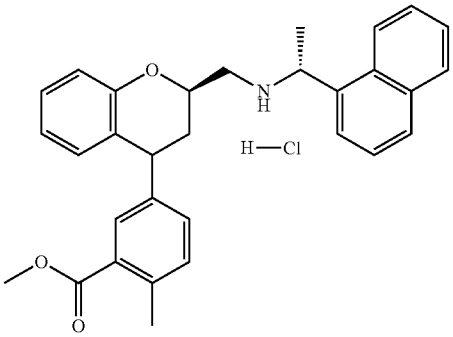

Methyl 5-((2R)-2-(((tert-butoxycarbonyl)((R)-1-(naphthalen-1-yl)ethyl)amino) methyl) chroman-4-yl)-2-methylbenzoate (300 g, 530 mmol, 1.0 eq) in methanol (1.2 L, 4.0 v) solution was heated to reflux (63° C.). Aqueous 6 N HCl (~352 mL, 2121 mmol, 4.0 eq) was added with a dropping funnel to the reaction mixture at 63° C. over a period of 2 h. The solution was allowed to stir at 63° C. for an additional one hour and cooled to 20° C. at −10° C./h rate and then allowed to stir at 20° C. for 7 h. The white suspension was filtered and the solid was washed first with methanol (225 mL, 0.75 v), then with water [2×300 mL (1 v)], affording methyl 2-methyl-5-((2R)-2-((((R)-1-(naphthalen-1-yl)ethyl)amino) methyl) chroman-4-yl)benzoate hydrochloride as a wet white hydrochloride salt. This product was ready for use in the next step of the synthesis.

Yield: 98%

Mass: 466.12 [MH+]

1H NMR (400 MHz, DMSO-d6) δ: 8.34-8.24 (m, 1H), 7.96-7.88 (m, 1H), 7.78 (d, J=8.1 Hz, 1H), 7.72 s (dd, J=7.2, 1.2 Hz, 1H), 7.63 (d, J=1.3 Hz, 1H), 7.56-7.44 (m, 3H), 7.27 (d, J=1.2 Hz, 2H), 7.06 (tdd, J=7.1, 2.0, 1.0 Hz, 1H), 6.79 (dd, J=8.2, 1.3 Hz, 1H), 6.71 (td, J=7.5, 1.3 Hz, 1H), 6.52 (dt, J=7.7, 1.4 Hz, 1H), 4.67 (q, J=6.5 Hz, 1H), 4.35-4.12 (m, 2H), 3.78 (s, 3H), 2.79 (dd, J=12.2, 6.1 Hz, 1H), 2.64 (dd, J=12.3, 5.4 Hz, 1H), 2.49 (s, 3H), 2.22 (ddd, J=13.5, 5.8, 1.7 Hz, 1H), 1.85-1.69 (m, 1H), 1.41 (d, J=6.5 Hz, 3H).

Step-8: 2-methyl-5-((2R,4S)-2-((((R)-1-(naphthalen-1-yl)ethyl)amino)methyl) chroman-4-yl)benzoic acid Hydrochloride Salt

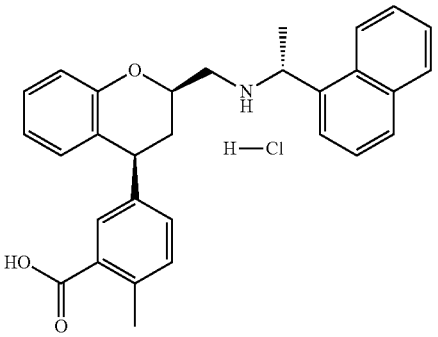

Methyl-2-methyl-5-((2R,4S)-2-((((R)-1-(naphthalen-1-yl)ethyl)amino) methyl) chroman-4-yl)benzoate hydrochloride (260 g, 518 mmol, 1.0 eq) was dissolved in a mixture of methanol (1.48 L, 5.7 v) and tetrahydrofuran (1.48 L, 5.7 v). The above solution was heated to 55° C., into that was added 10 N NaOH (~260 mL, 2589 mmol, 5.0 eq) over a period of 20 min. The clear solution was allowed to stir at 55° C. for 2 h (pH 10). The reaction mixture was cooled to 30° C. and diluted with water (1.82 L, 7.0 v). Aqueous HCl 2 N (1062 mL, 2124 mmol, 4.1 eq.) was slowly added to adjust the pH to 6-7. The zwitterion was precipitated and the suspension was cooled to 20° C. and allowed to stir at this temperature for 30 min. The sandy solid was easily filtered, washed first with water [2×1300 mL (5 v)] and then with EtOH (520 mL, 2.0 v) followed by isopropyl alcohol (IPA) (260 mL, 1.0 v). The white solid was dried at 40° C. in vacuo for 20 h to afford 2-methyl-5-((2R,4S)-2-((((R)-1-(naphthalen-1-yl)ethyl)amino)methyl) chroman-4-yl)benzoic acid (crude, 225 g).

Yield: 96.15%
Purity: 83.79:15.57%

Purification: The crude 2-methyl-5-((2R,4S)-2-((((R)-1-(naphthalen-1-yl)ethyl)amino)methyl) chroman-4-yl)benzoic acid (225 g, 498 mmol, 1.0 eq) was suspended in a 5:1 ethanol/dichloromethane solvent mixture (5.4 L, 24.0 v). The suspension was heated to vigorous refluxing (60° C.) to complete dissolution of the material. The subsequent recrystallization began before the end of the dissolution. The suspension was allowed to stir at 60° C. for 10 min and then was cooled to 20° C. at a −20° C./h rate, filtered, washed first with 5:1 ethanol/dichloromethane solvent mixture (2×675 mL, 3 v), then with ethanol (225 mL, 1 v). The white solid was dried at 40° C. overnight to afford 2-methyl-5-((2R,4S)-2-((((R)-1-(naphthalen-1-yl)ethyl)amino)methyl) chroman-4-yl)benzoic acid as a white solid.

Yield:64.1% (150 g)
Purity: 99.70:0.20%

Hydrochloride salt preparation: The diastereomerically pure 2-methyl-5-((2R,4S)-2-((((R)-1-(naphthalen-1-yl)ethyl)amino)methyl) chroman-4-yl)benzoic acid (150 g, 332 mmol, 1.0 eq) thus obtained was suspended in water (2.55 L, 17 v). After heating the reaction mass to 30° C., a solution of 2 N aqueous NaOH (~300 mL, 598 mmol, 1.8 eq) was added quickly, leading to complete dissolution of the compound. The solution was filtered through a GF/A glass microfiber filter in order to remove any solid impurity. Afterwards, 2 N aqueous HCl was added (665 mL, 1329 mmol, 4 eq) at the same temperature, inducing precipitation of a voluminous white solid difficult to stir. The reaction mass was allowed to stir at ambient temperature (22° C.) for 20 h. The resulting slurry was filtered, washed with water until the pH of the filtrate became 6 [1500 mL (10 v) then 3×600 mL (4 v)]. After 65 h at 40° C. in a drying oven, 2-methyl-5-((2R,4S)-2-((((R)-1-(naphthalen-1-yl)ethyl) amino)methyl) chroman-4-yl)benzoic acid hydrochloride salt was obtained as a white solid in a quantitative yield.

Yield: 89.53%
Purity: 99.63%
Mass: 452.18 [MH+]

1H NMR (DMSO-d6) δ: 12.76 (bs, 1H), 10.07 (bs, 1H), 9.64 (bs, 1H), 8.30 (d, J=8.4 Hz, 1H), 8.14-7.93 (m, 3H), 7.73-7.56 (m, 4H), 7.33-7.20 (m, 2H), 7.14 (t, J=7.6 Hz, 1H), 6.87 (dd, J=8.2, 1.0 Hz, 1H), 6.79 (td, J=7.6, 1.1 Hz, 1H), 6.57 (d, J=7.7 Hz, 1H), 5.48 (bs, 1H), 4.68 (m, 1H), 4.29 (dd, J=12.0, 5.7 Hz, 1H), 3.30 (d, J=8.6 Hz, 1H), 3.20 (d, J=12.8 Hz, 1H), 2.48 (s, 3H), 2.24 (dd, J=12.7, 5.3 Hz, 1H), 1.92 (q, J=12.1 Hz, 1H), 1.77 (d, J=6.6 Hz, 3H).

IR (KBr, cm-1): 3057.55, 2956.04, 2876.08, 2767.21, 2681.29, 2499.80, 2481.85, 2298.48, 2202.11, 1711.42, 1595.25, 1579.33, 1517.30, 1497.94, 1483.60, 1451.74, 1400.13, 1379.30, 1362.67, 1300.55, 1279.31, 1238.73, 1217.88, 1187.99, 1175.75, 1118.41, 1089.60, 1072.72, 1020.79, 972.36, 928.79, 913.23, 892.94, 860.86, 797.19, 780.99, 745.77, 704.12, 667.76, 611.33, 571.04, 543.00, 528.59, 470.53, 435.58, 416.04, 401.77.

PXRD (x-ray powder diffraction pattern) peaks in Table 1 are tabulated from those shown in FIG. 1.

TABLE 1

PXRD peaks (2-theta, and corresponding D spacing) of diastereomerically pure 2-methyl-5-((2R,4S)-2-((((R)-1-(naphthalen-1-yl)ethyl)amino)methyl) chroman-4-yl) benzoic acid hydrochloride salt

| [°2Θ] | D spacing |
|---|---|
| 6.6358 | 13.32047 |
| 9.7531 | 9.06885 |
| 13.7400 | 6.44504 |
| 15.1585 | 5.84496 |
| 15.3484 | 5.77309 |
| 17.8145 | 4.97908 |
| 18.3030 | 4.84728 |
| 18.9897 | 4.67350 |
| 19.5651 | 4.53735 |
| 20.9357 | 4.24328 |
| 22.4292 | 3.96401 |
| 23.2535 | 3.82532 |
| 23.7416 | 3.74777 |
| 25.1969 | 3.53451 |
| 27.3036 | 3.26640 |

Figure 2:
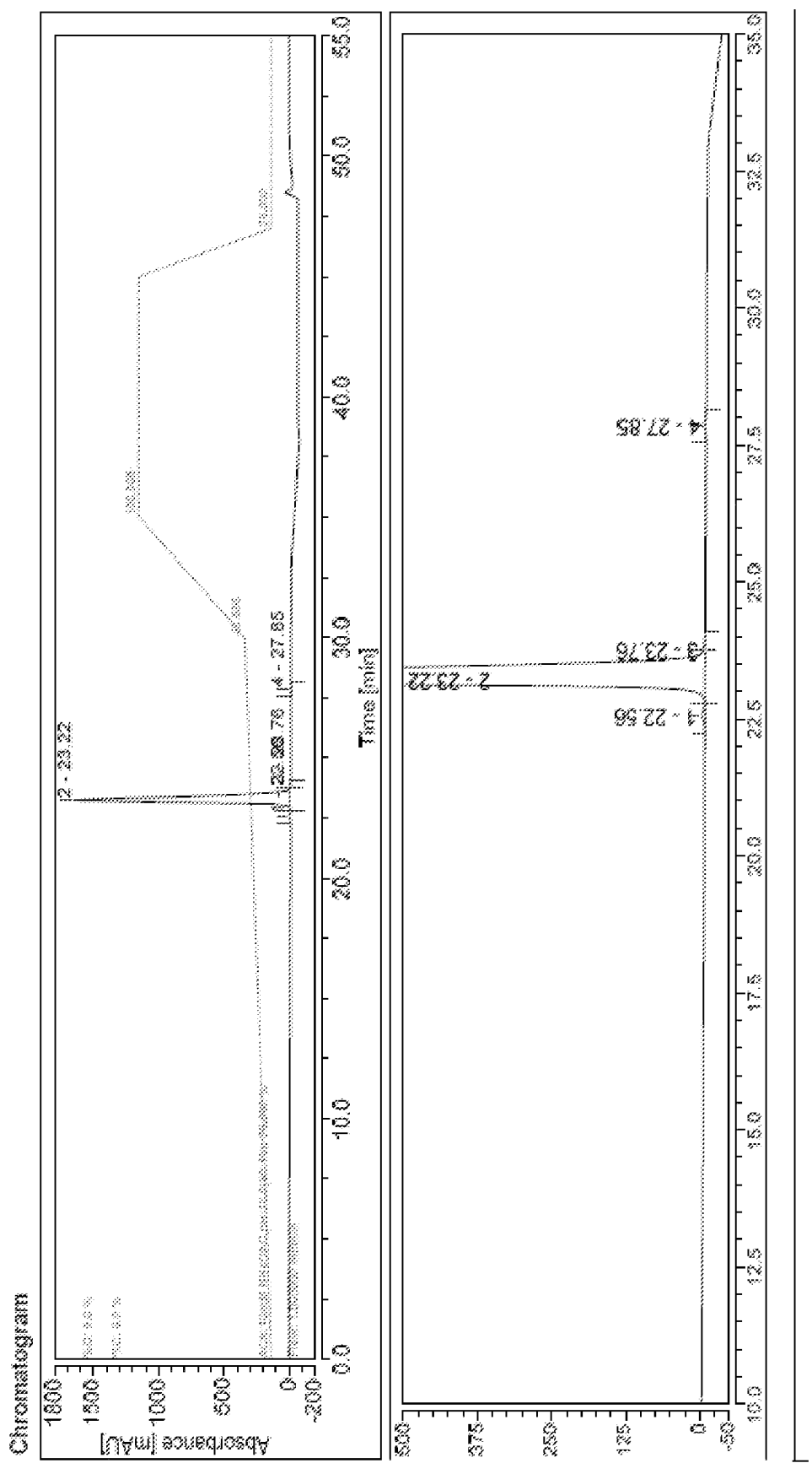
FIG. 2 is an example HPLC chromatogram regarding Compound-A and Compound-B, which were made by a representative synthesis route of this disclosure. Corresponding peak table is presented in Table 2 below.
Figure 3:
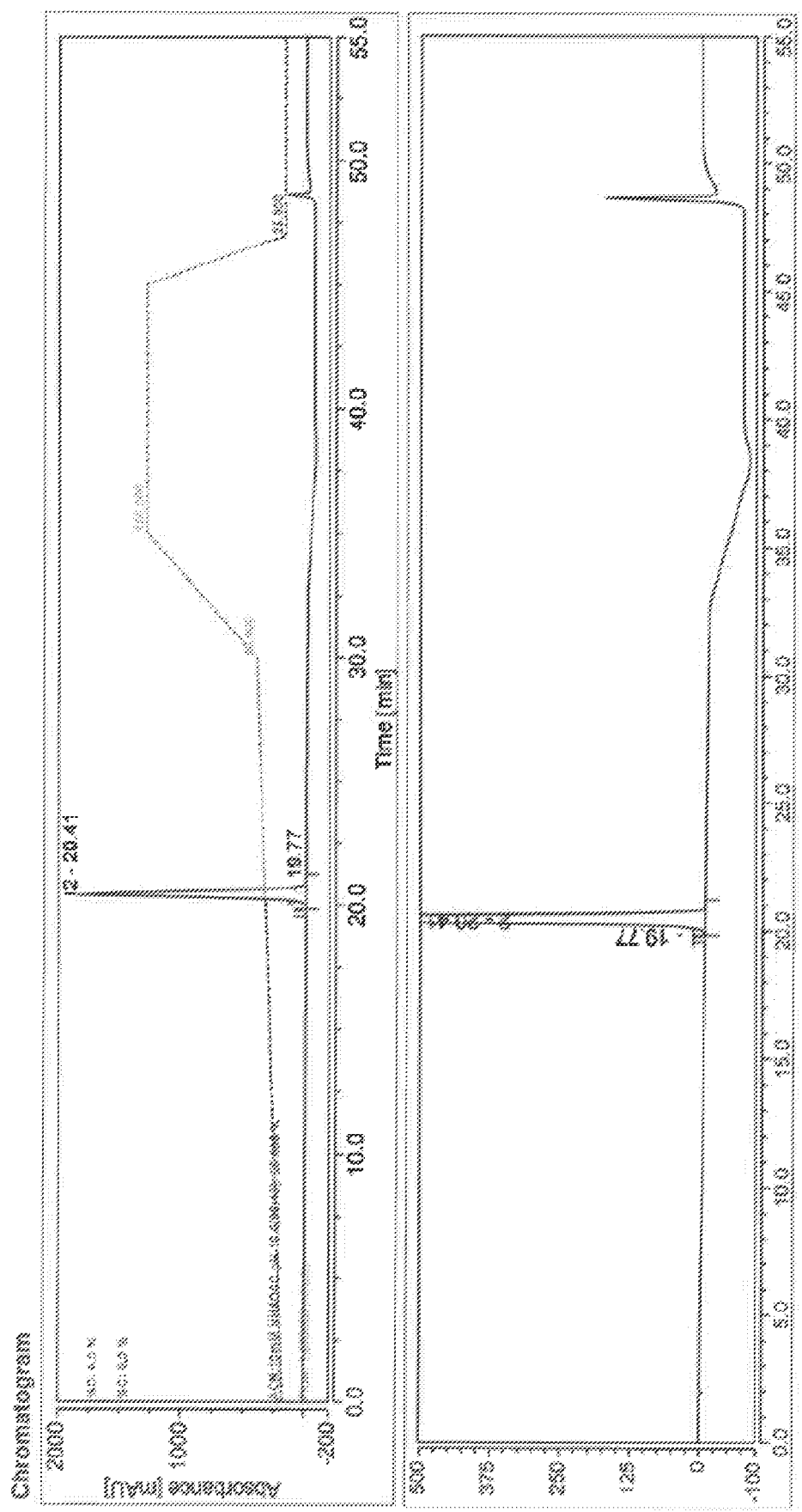
FIG. 3 is an example HPLC chromatogram regarding Compound-A and Compound-B, which were made by a representative synthesis route of this disclosure. Corresponding peak table is presented in Table 3 below.

As previously discussed, the amounts of impurities can be measured using HPLC (including RP-HPLC, HPLC-MS, HPLC-MS/MS, HPLC-UV, and IEX) per methods understood in the art. For example, FIGS. 2 and 3 shows example HPLC chromatograms, and the corresponding peak tables are presented in Tables 2 & 3, respectively. Each peak table discloses information regarding Compound-A and Compound-B.

TABLE 2

PEAK TABLE FOR FIG. 2
Peak Table

| No. | Peak Name | Retention Time | Rel. Ret. time | Area (mAU*sec) | Rel Area % |
|---|---|---|---|---|---|
| 1 | Compound-B | 22.56 | 0.97 | 58517 | 0.23 |
| 2 | Compound-A | 23.22 | 1.00 | 25617895 | 99.54 |

TABLE 3

PEAK TABLE FOR FIG. 3
Peak Table

| No. | Peak Name | Retention Time | Rel. Ret. time | Area (mAU*sec) | Rel Area % |
|---|---|---|---|---|---|
| 1 | Compound-B | 19.77 | 0.97 | 2764 | 0.01 |
| 2 | Compound-A | 20.41 | 1.00 | 27496733 | 99.99 |

Below is the RP-HPLC experimental details related to FIGS. 2 and 3:
RP-HPLC: Column: YMC Triart (250×4.6) mm,5 μm;
Run Time (min): 55.00; Injection Volume: 5.00 μL;
Wavelength: WVL:220 nm; Flow Rate:1.00 ml/min; Column temp 40.0° C.;

Mobile Phase A: 10 mM NH₄OAc, pH-10.0: ACN (90:10); and

Mobile Phase B: CAN:10 mM NH₄OAc, pH-10.0 (90:10).

In some embodiments, this disclosure provides for:

A1. A method for synthesizing Compound-A,

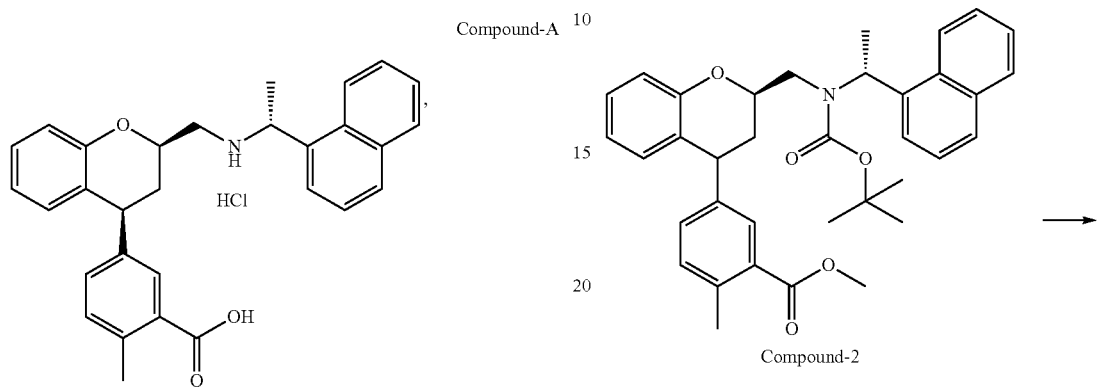

wherein the synthesis does not involve pyrophoric reagents.

A2. The method of A1, wherein the synthesis comprises the steps of:

1) reducing Compound-1 by using 5% Pd/C and ammonium formate under heating at 33° C. to 34° C. in methanol-ethyl acetate solvent system to give Compound-2

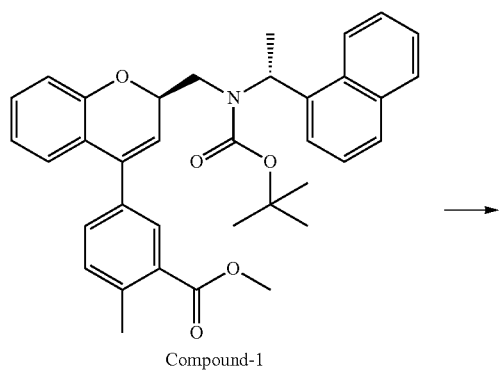

2) deprotecting the Boc protected amine group of Compound-2, by refluxing Compound-2 with 6 N HCl in methanol to give Compound-3

3) hydrolyzing the ester group of Compound-3, by heating the Compound-3 at 55° C. with NaOH in methanol-THF to give crude Compound-4, further the obtained crude compound was purified by recrystallization using ethanol:DCM (5:1) solvent system followed by recrystallization using isopropanol to yield diastereomerically pure Compound-4

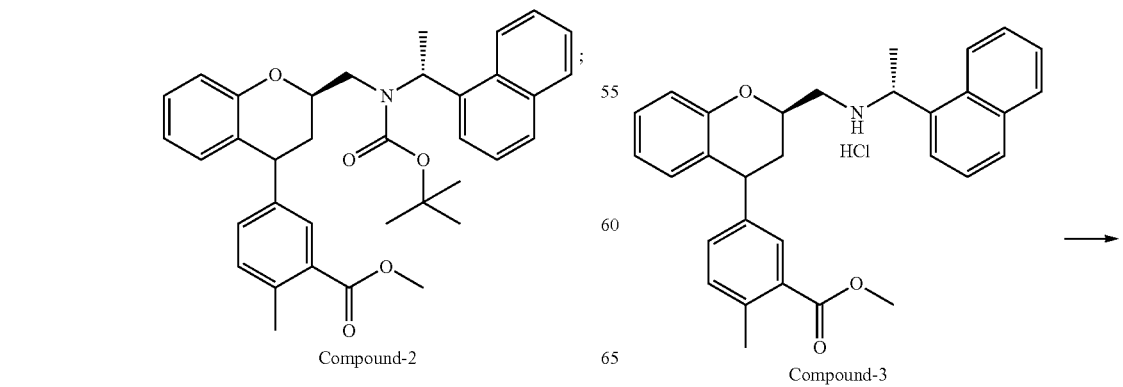

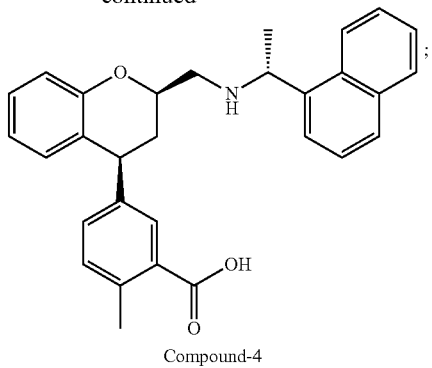

Compound-4

4) converting the Compound-4 to its hydrochloride salt (Compound-A) using 2 N aqueous HCl.

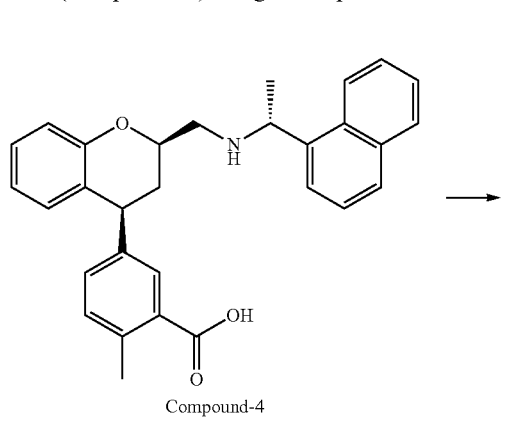

Compound-4

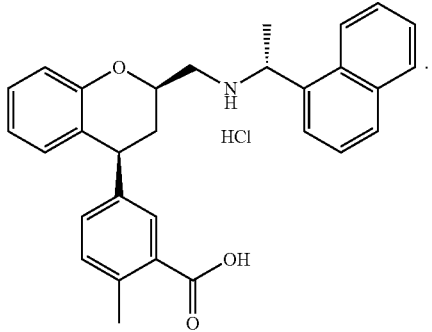

Compound-A

A3. A method of synthesizing Compound-1, the method comprising:
a) reducing the amide group of Compound-5 using sodium bis(2-methoxyethoxy)aluminium hydride (such as the sodium bis(2-methoxyethoxy)aluminium hydride known by the brand name Vitride™) in toluene followed by hydrochloride salt formation using concentrated HCl to give Compound-6

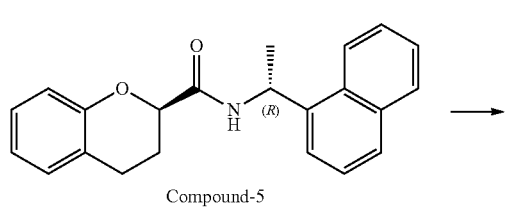

Compound-5

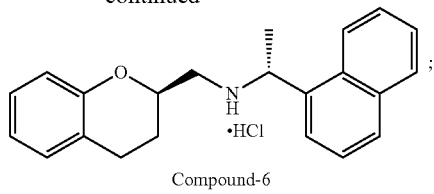

Compound-6 b) protecting the free amino group of Compound-6 using Boc anhydride (Di-tert-butyl dicarbonate) and tripotassium phosphate to give Compound-7

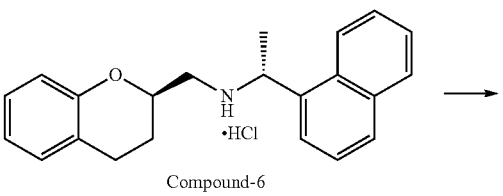

Compound-6

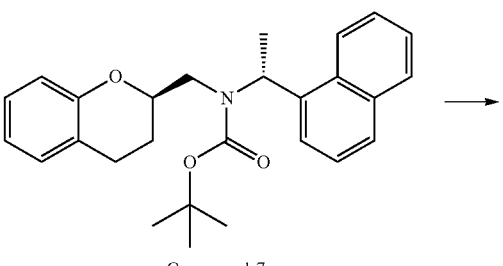

Compound-7 c) oxidizing Compound-7 using KMnO$_4$ and MgSO$_4$ to give Compound-8

Compound-7

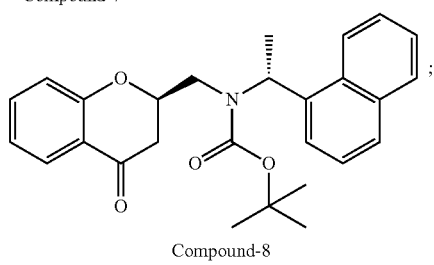

Compound-8 d) reacting Compound-8 with a triflating agent to give Compound-9

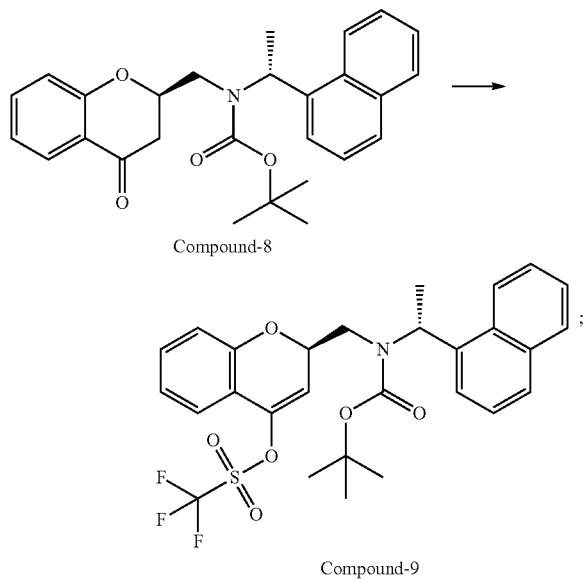

Compound-8

Compound-9 e) coupling of Compound-9 with methyl 2-methyl-5-(4,4,5,5-tetramethyl-1,3,2-dioxaborolan-2-yl)benzoate in the presence of a palladium catalyst to give Compound-1

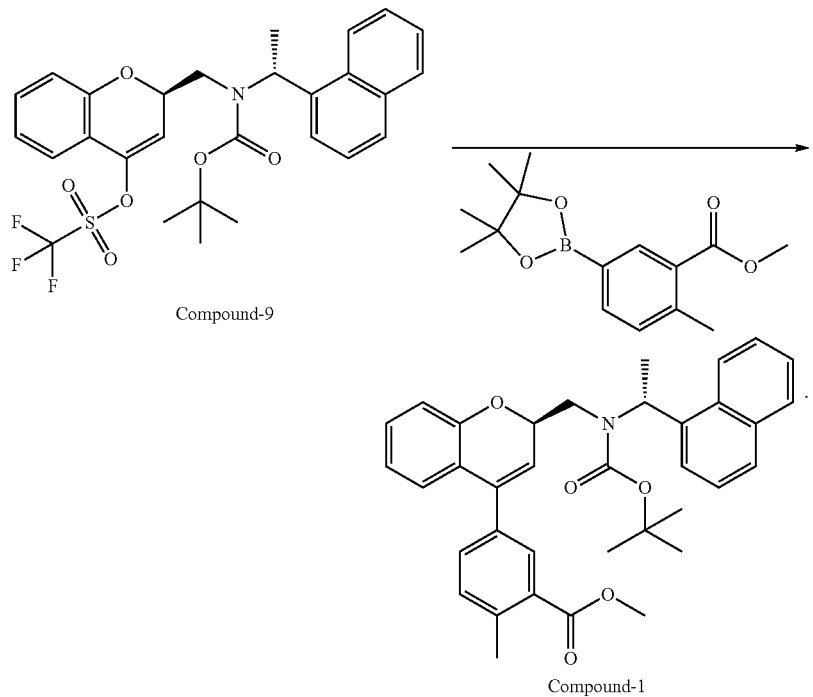

Compound-9

Compound-1

A4. The method of A1, wherein the synthesis does not involve a column chromatography purification step to obtain the product.

A5. The method of A1, wherein the synthesis does not involve a pyrophoric reagent.

A6. The method of A1, wherein the synthesis does not involve added hydrogen gas.

A7. The method of A1, wherein the synthesis is performed at scales of 1 kg, 10 kg, or 100 kg.

A8. The method of A4, wherein the synthesis does not involve a chiral column chromatography purification method to obtain the product.

A9. The method of A4, wherein the synthesis does not involve a pyrophoric reagent.

A10. A method of A method of obtaining a substantially diastereomerically pure composition of a compound 4, comprising: crystallizing said compound 4 from a mixture of a methyl ester compound 3 and compound 4 under appropriate crystallization conditions.

The invention described and claimed herein has many attributes and embodiments including, but not limited to, those set forth or described or referenced in this Detailed Disclosure. It is not intended to be all-inclusive and the invention described and claimed herein are not limited to or by the features or embodiments identified in this Detailed Disclosure, which is included for purposes of illustration only and not restriction. A person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, and other referenced materials or documents. Reference to any applications, patents and publications in this specification is not, and should not be taken as, an acknowledgment or any form of suggestion that they constitute valid prior art or form part of the common general knowledge in any country in the world.

The specific methods, processes and compounds described herein are representative of preferred embodiments and are exemplary and not intended as limitations on the scope of the invention. Other objects, embodiments, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of this, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document, and should not be read as limiting the scope of this. Any examples of embodiments, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although this has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any patient matter from the genus, regardless of whether or not the excised material is specifically recited herein.

Other embodiments are within the following claims. In addition, where features or embodiments of the invention are described in terms of Markush groups, those skilled in the art will recognize that the invention is also thereby described in terms of any individual member or subgroup of members of the Markush group.

What is claimed is:

1. A method for the manufacture of 2-methyl-5-((2R,4S)-2-((((R)-1-(naphthalen-1-yl) ethyl) amino) methyl) chroman-4-yl) benzoic acid hydrochloride (Compound-A),

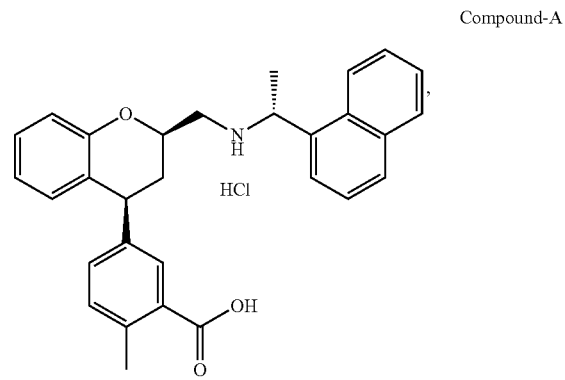 [SMILES: Cc1ccc([C@@H]2C[C@H](CN[C@H](C)c3cccc4ccccc34)Oc3ccccc32)cc1C(=O)O ; Cl]

Compound-A wherein the synthesis includes the steps of:
a) reducing methyl 5-((R)-2-(((tert-butoxycarbonyl) ((R)-1-(naphthalen-1-yl) ethyl) amino) methyl)-2H-chromen-4-yl)-2-methylbenzoate (Compound-1) using Pd/C and ammonium formate to give methyl 5-((2R)-2-(((tert-butoxycarbonyl) ((R)-1-(naphthalen-1-yl) ethyl) amino) methyl) chroman-4-yl)-2-methylbenzoate (Compound-2)

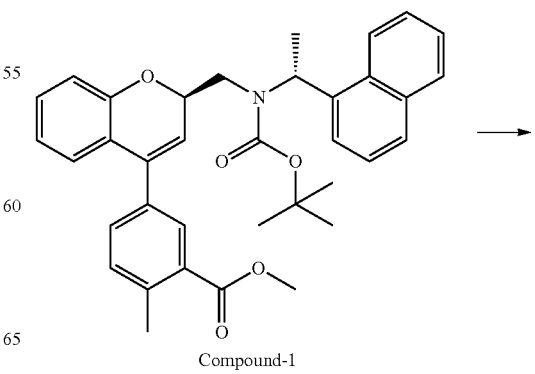

Compound-1

-continued

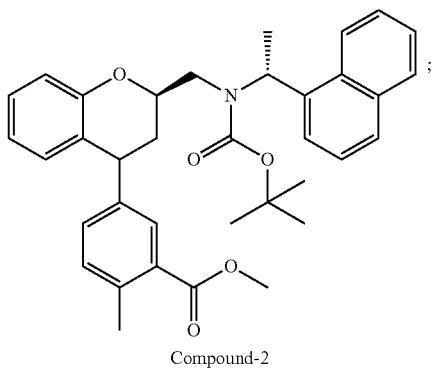

Compound-2 b) carrying out a Boc-deprotection reaction of Compound-2 to give the corresponding amino methyl 2-methyl-5-((2R)-2-((((R)-1-(naphthalen-1-yl) ethyl) amino) methyl) chroman-4-yl) benzoate hydrochloride (Compound-3)

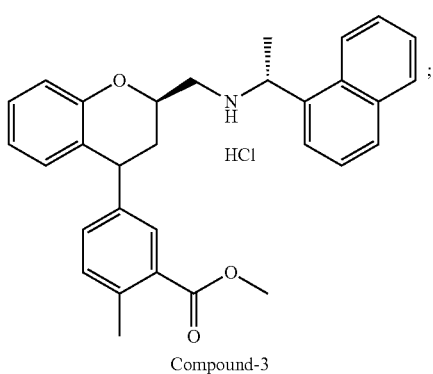

Compound-2 c) hydrolyzing the ester group of Compound-3 and isolating the pure diastereoisomer by using recrystallization to give 2-methyl-5-((2R,4S)-2-((((R)-1-(naphthalen-1-yl) amino) methyl) chroman-4-yl) benzoic acid (Compound-4)

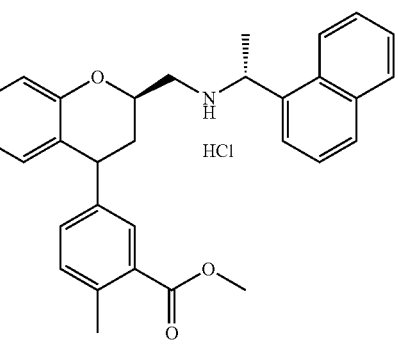

Compound-3

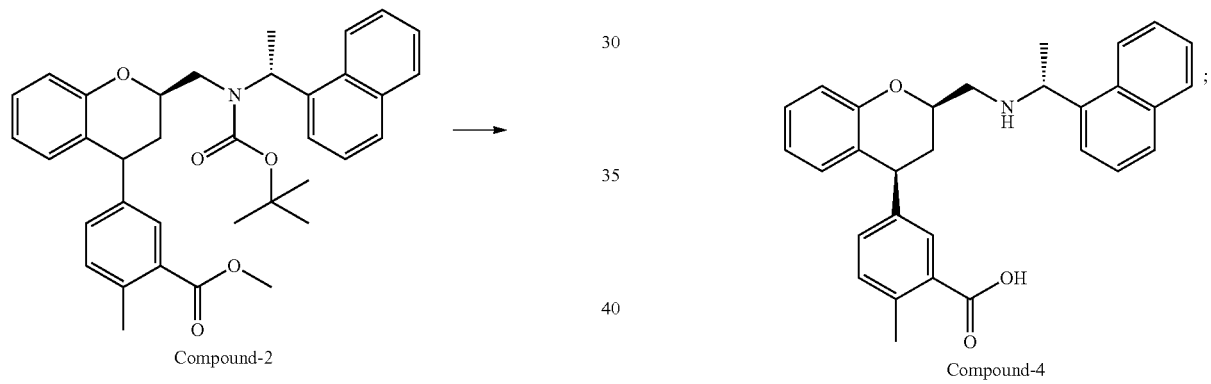

Compound-4 and d) converting Compound-4 to its hydrochloride salt

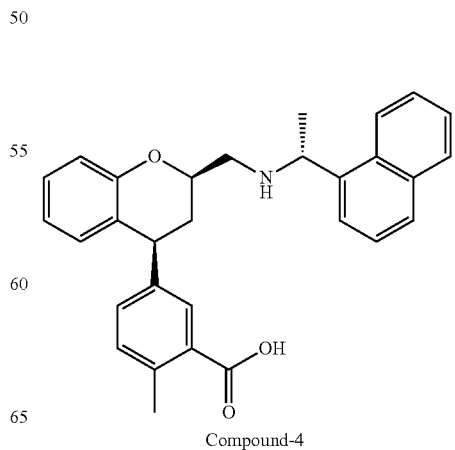

Compound-4

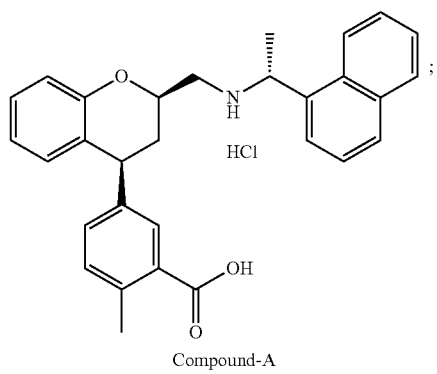

Compound-A and further comprising a method for the manufacture of methyl 5-((R)-2-(((tert-butoxycarbonyl) ((R)-1-(naphthalen-1-yl) ethyl) amino) methyl)-2/-chromen-4-yl)-2-methylbenzoate (Compound-1) which comprises:

A) reducing the amide group of (R)-N-((R)-1-(naphthalen-1-yl) ethyl) chroman-2-carboxamide (Compound-5) using sodium bis(2-methoxyethoxy) aluminium hydride, followed by acid treatment, to give (R)-N-((R)-chroman-2-ylmethyl)-1-(naphthalen-1-yl) ethanamine hydrochloride (Compound-6)

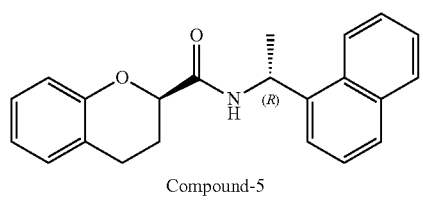

Compound-5

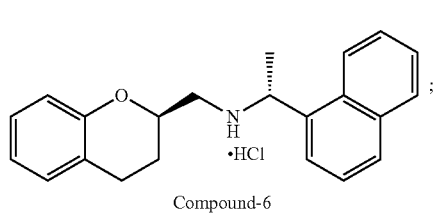

Compound-6

B) protecting the free amino group of Compound-6 to give tert-butyl ((R)-chroman-2-ylmethyl) ((R)-1-(naphthalen-1-yl) ethyl) carbamate (Compound-7)

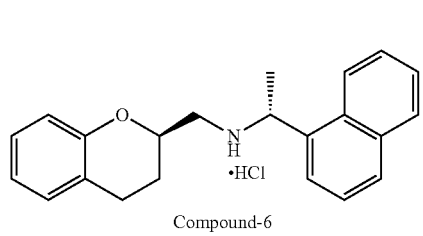

Compound-6

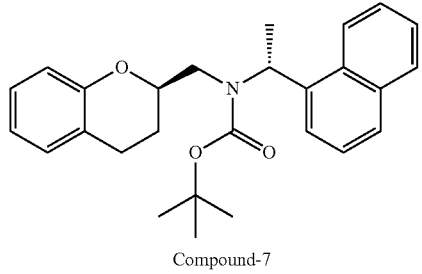

Compound-7

C) oxidizing Compound-7 to give tert-butyl ((R)-1-(naphthalen-1-yl) ethyl) (((R)-4-oxochroman-2-yl) methyl) carbamate (Compound-8)

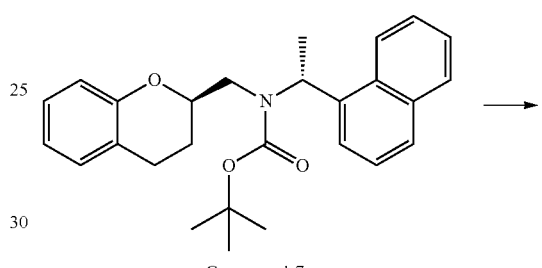

Compound-7

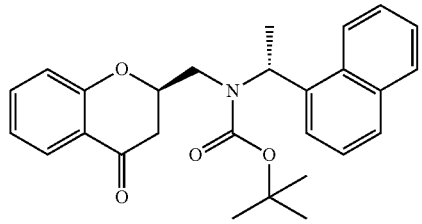

Compound-8

D) reacting Compound-8 with a triflating agent to give (R)-2-(((tert-butoxycarbonyl) ((R)-1-(naphthalen-1-yl) ethyl) amino) methyl)-2H-chromen-4-yl trifluoromethanesulfonate (Compound-9)

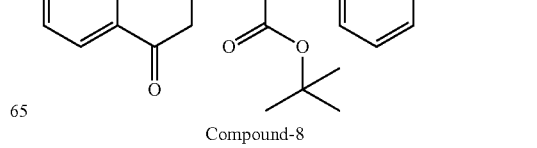

Compound-8

-continued

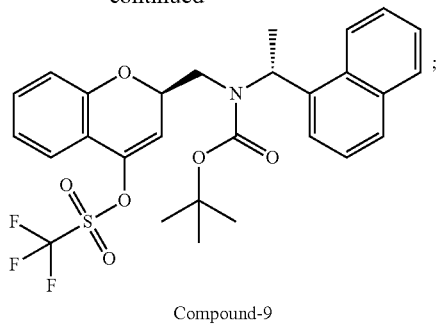

Compound-9 and

E) coupling of Compound-9 with methyl 2-methyl-5-(4,4,5,5-tetramethyl-1,3,2-dioxaborolan-2-yl) benzoate to give methyl5-((R)-2-(((tert-butoxycarbonyl) ((R)-1-(naphthalen-1-yl) ethyl) amino) methyl)-2H-chromen-4-yl)-2-methylbenzoate (Compound-1)

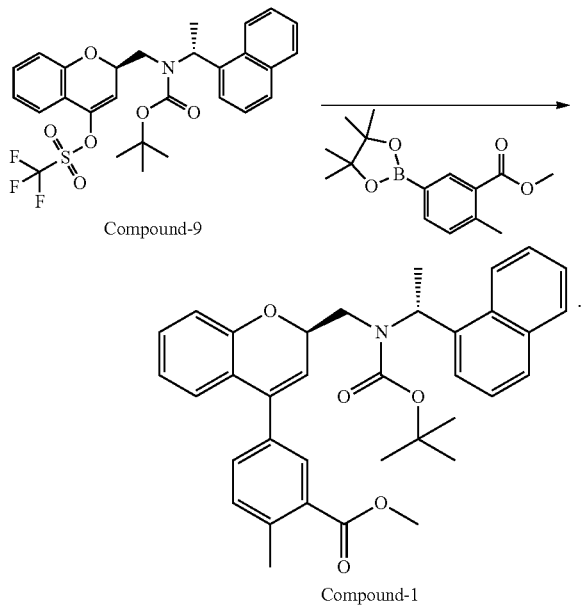

2. The method of claim 1, wherein the Compound-A is present with less than 1.0% area by HPLC of the impurity 2-methyl-5-((2R, 4R)-2-((((R)-1-(naphthalen-1-yl) ethyl) amino) methyl) chroman-4-yl) benzoic acid hydrochloride (Compound-B).

3. The method of claim 2, wherein the level of the impurity 2-methyl-5-((2R,4R)-2-((((R)-1-(naphthalen-1-yl) ethyl) amino) methyl) chroman-4-yl) benzoic acid hydrochloride (Compound-B) is less than 0.5% area by HPLC.

4. The method of claim 1, wherein the step (c) hydrolyzing the ester group of Compound-3 and isolating the pure diastereoisomer by using recrystallization is performed by heating Compound-3 at 55° C. with 10 N NaOH in methanol-THF to give crude Compound-4, which is further purified by recrystallization to give diastereomerically pure Compound-4.

5. The method of claim 1, wherein step (A) reducing the amide group of (R)-N-((R)-1-(naphthalen-1-yl) ethyl) chroman-2-carboxamide (Compound-5) using sodium bis(2-methoxyethoxy) aluminium hydride is performed using sodium bis(2-methoxyethoxy) aluminium hydride in toluene solution, followed by acid treatment using hydrochloride concentrated HCl.

6. The method of claim 1, wherein step (c) isolating the pure diastereoisomer by using recrystallization is performed using a solvent mixture consisting of a protic polar solvent and an aprotic polar solvent.

7. The method of claim 6, wherein the protic polar solvent is ethanol, methanol or isopropanol.

8. The method of claim 6, wherein the aprotic polar solvent is dichloromethane, dimethylformamide or tetrahydrofuran.

9. The method of claim 6, wherein the solvent mixture is ethanol: dichloromethane solvent mixture.

10. The method of claim 9, wherein the solvent mixture is a mixture ranging from 5:1 to 1:5 ethanol: dichloromethane (v/v) solvent mixture.

* * * * *